US009284343B2

(12) United States Patent
Beaucage et al.

(10) Patent No.: US 9,284,343 B2
(45) Date of Patent: Mar. 15, 2016

(54) 2'-O-AMINOOXYMETHYL NUCLEOSIDE DERIVATIVES FOR USE IN THE SYNTHESIS AND MODIFICATION OF NUCLEOSIDES, NUCLEOTIDES AND OLIGONUCLEOTIDES

(75) Inventors: Serge L. Beaucage, Silver Spring, MD (US); Jacek Cieslak, Kensington, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 56 days.

(21) Appl. No.: 14/008,805

(22) PCT Filed: Mar. 29, 2012

(86) PCT No.: PCT/US2012/031107
§ 371 (c)(1),
(2), (4) Date: Oct. 29, 2013

(87) PCT Pub. No.: WO2012/138530
PCT Pub. Date: Oct. 11, 2012

(65) Prior Publication Data
US 2014/0051846 A1 Feb. 20, 2014

Related U.S. Application Data

(60) Provisional application No. 61/471,451, filed on Apr. 4, 2011.

(51) Int. Cl.
C07H 21/00 (2006.01)
C07H 19/16 (2006.01)
C07H 19/00 (2006.01)
C07H 19/06 (2006.01)
C07H 23/00 (2006.01)
C07H 1/00 (2006.01)
C07H 19/048 (2006.01)

(52) U.S. Cl.
CPC .............. *C07H 19/16* (2013.01); *C07H 1/00* (2013.01); *C07H 19/048* (2013.01); *C07H 19/06* (2013.01); *C07H 23/00* (2013.01)

(58) Field of Classification Search
CPC ........ C07H 19/06; C07H 10/06; C07H 19/16; C07H 23/00; C07H 1/00; C07H 19/048
See application file for complete search history.

(56) References Cited

U.S. PATENT DOCUMENTS

| 6,127,533 | A | 10/2000 | Cook et al. |
| 6,194,598 | B1 | 2/2001 | Cook et al. |
| 6,576,752 | B1 | 6/2003 | Manoharan et al. |
| 6,825,331 | B2 | 11/2004 | Manoharan et al. |
| 6,849,723 | B2 * | 2/2005 | Cook et al. ............. 536/22.1 |
| 7,368,550 | B2 | 5/2008 | Dellinger et al. |
| 2003/0181693 | A1 | 9/2003 | Cook et al. |
| 2004/0014108 | A1 | 1/2004 | Eldrup et al. |
| 2004/0014957 | A1 | 1/2004 | Eldrup et al. |
| 2009/0258931 | A1 | 10/2009 | Monia et al. |
| 2010/0324277 | A1 | 12/2010 | Bhat et al. |

OTHER PUBLICATIONS

Beaucage et al., "Advances in the Synthesis of Oligonucleotides by the Phosphoramidite Approach," *Tetrahedron*, 48 (12), 2223-2311 (1992).
Beaucage et al., "The Synthesis of Modified Oligonucleotides by the Phosphoramidite Approach and Their Applications," *Tetrahedron*, 49 (28), 6123-6194 (1993).
Cieślak et al., "Permanent or reversible conjugation of 2'-O- or 5'-O-aminooxymethylated nucleosides with functional groups as a convenient and efficient approach to the modification of RNA and DNA sequences," *Nucl. Acids Res.*, 40 (5), 2312-2329 (2012) with supporting information.
Cieślak et al., "The 2-cyano-2,2-dimethylethanimine-*N*-oxymethyl group for the 2'-hydroxyl protection of ribonucleosides in the solid-phase synthesis of RNA sequences," *Chemistry*, 19 (14), 4623-4632 (2013).
Cieślak et al., "The 4-(N-dichloroacetyl-N-methylamino)benzyloxymethyl group for 2'-hydroxyl protection of ribonucleosides in the solid-phase synthesis of oligoribonucleotides," *J. Org. Chem.*, 73, 2774-2783 (2008).
Fuoss, "Ionic Association. I. Derivation of Constants from Conductance Data," *J. Am. Chem. Soc.*, 79 (13), 3448-3451 (1957).
International Preliminary Report on Patentability, Application No. PCT/US2012/031107, dated Oct. 8, 2013.
International Search Report, Application No. PCT/US2012/031107, dated Oct. 11, 2012.

(Continued)

*Primary Examiner* — Lawrence E Crane
(74) *Attorney, Agent, or Firm* — Leydig, Voit & Mayer, Ltd.

(57) ABSTRACT

Disclosed are O-protected compounds of the formula (I):

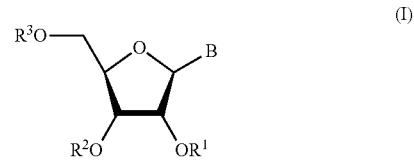

(I)

wherein B is an optionally protected nucleobase, and $R^1$-$R^3$ are as described herein, wherein at least one of $R^1$-$R^3$ is —$CH_2$—O—N=CHR. The compounds are useful as intermediates in oligonucleotide synthesis. Also disclosed is a method of preparing the compounds from nucleosides via a process comprising conversion of a hydroxyl group to a methylthiomethoxy group, and a method of preparing oligonucleotides such as RNA starting from the compounds. The —$CH_2$—O—N=CHR group is stable during oligonucleotide synthesis and can be easily removed after synthesis via, for example, treatment with a base.

15 Claims, 13 Drawing Sheets

(56) References Cited

OTHER PUBLICATIONS

Iyer, "Nucleobase Protection of Deoxyribo- and Ribonucleosides," *Current Protocols in Nucleic Acid Chem.*, 1, 2.1.1-2.1.17 (2000).

Maraval et al., "A Straightforward Synthesis of N-Functionalized β-Diimines," *Eur. J. Org. Chem.*, 385-394 (2003).

McBride et al., "Amidine Protecting Groups of Oligonucleotide Synthesis," *J. Am. Chem. Soc.*, 108 (8), 2040-2048 (1986).

Ogilvie et al., "Total chemical synthesis of a 77-nucleotide-long RNA sequence having methionine-acceptance activity," *Proc. Natl. Acad. Sci. USA*, 85, 5764-5768 (1988).

Otter et al., "Benzopyrylium Salts. V. Preparation and Properties of Substituted 2,3-Diphenylbenzopyrylium Perchlorates," *J. Am. Chem. Soc.*, 73 (3), 973-975 (1951).

Reetz et al., "Trimethylsilyl Cyanide Promoted Cyanation of Tertiary Alkyl Chlorides and other SN1 Active Compounds," *Tetrahedron*, 39 (6), 961-965 (1983).

Seidan et al., "Mechanism of Racemization of Complex Ions. V. The Dissociation and Racemization of Tris-(2,2'-bipyridine)-iron (II) and Tris-(1,10-phenanthroline)-iron (II) Ions in Water-Methanol and Methanol Solutions," *J. Am. Chem. Soc.*, 81 (15), 4328-4335 (1959).

Semenyuk et al., "Synthesis of RNA using 2'-*O*-DTM protection," *J. Am. Chem. Soc.*, 128, 12356-12357 (2006).

Sun et al., "Highly Efficient Chemoselective Deprotection of *O*,*O*-Acetals and *O*,*O*-Ketals Catalyzed by Molecular Iodine in Acetone," 69, 8932-8934 (2004).

Written Opinion of the International Searching Authority, Application No. PCT/US2012/031107, dated Oct. 4, 2013.

\* cited by examiner

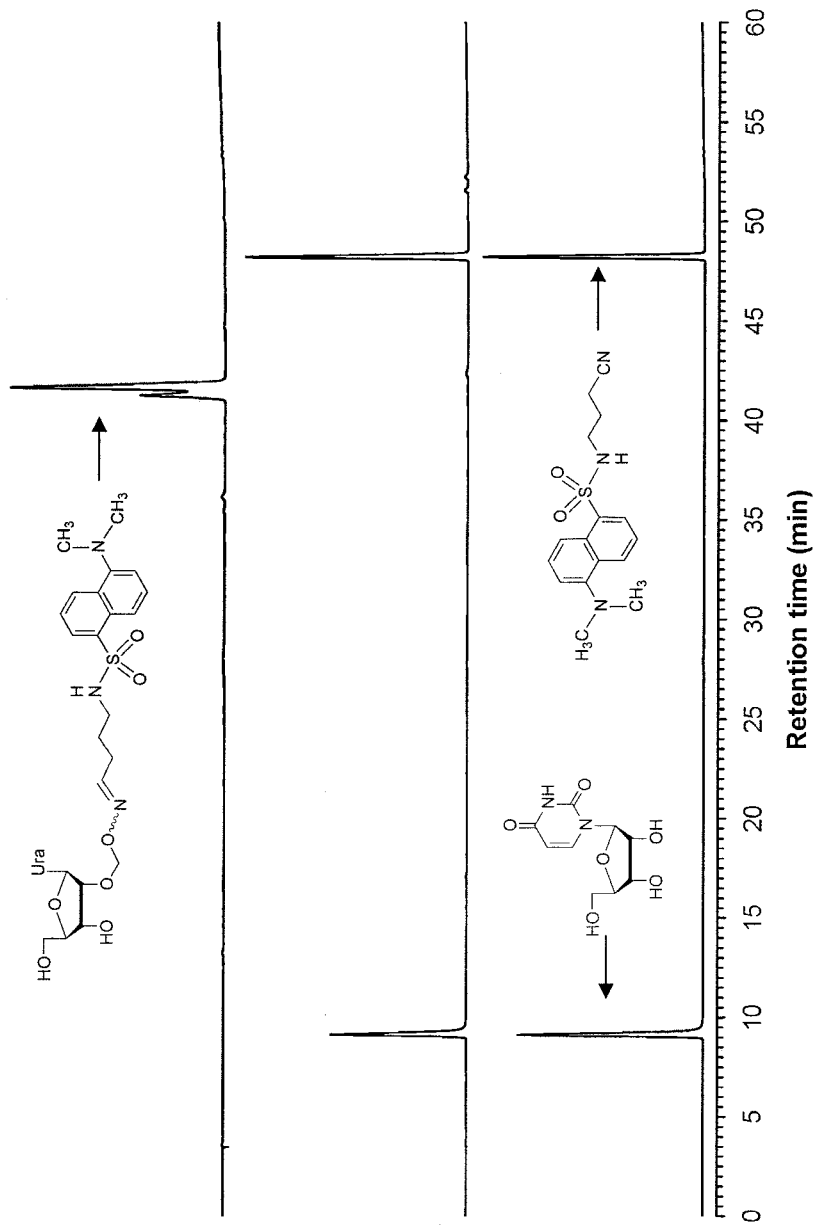

2'-O-AMINOOXYMETHYL NUCLEOSIDE DERIVATIVES FOR USE IN THE SYNTHESIS AND MODIFICATION OF NUCLEOSIDES, NUCLEOTIDES AND OLIGONUCLEOTIDES

CROSS-REFERENCE TO RELATED APPLICATIONS

This application is the U.S. national phase of International Application No. PCT/US2012/031107, filed on Mar. 29, 2012, which claims the benefit of U.S. provisional patent application No. 61/471,451, filed Apr. 4, 2011, the disclosures of which are incorporated by reference.

INCORPORATION-BY-REFERENCE OF MATERIAL ELECTRONICALLY FILED

Incorporated by reference in its entirety herein is a computer-readable nucleotide/amino acid sequence listing and identified as follows: One 725 Byte ASCII (Text) file named "714361_ST25(2).txt," created on Sep. 21, 2015.

BACKGROUND OF THE INVENTION

Recent developments in silencing the expression of specific genes, through RNA interference pathways, have led to an increased demand for synthetic RNA sequences and have created a pressing need for rapid and efficient methods for RNA synthesis. Some of the requirements for the production of RNA sequences in sufficient quantity and purity for pharmaceutical applications are those related to the design and implementation of hydroxyl protecting groups, which have historically been demonstrated to be of critical importance in RNA synthesis. Furthermore, chemical modifications of the hydroxyl function of ribonucleosides have been extensively investigated in order to identify the biophysical and biochemical parameters that are necessary for effective and lasting RNA interference-mediated gene silencing activities. For example, 2'-hydroxy modifications impart high binding affinity to RNA sequences, increased lipophilicity, enhanced chemical stability and nuclease resistance. The 2'-hydroxy group of ribonucleosides is also an attractive function for ligand attachment; there are numerous examples of ribonucleoside 2'-conjugates that have been reported in addition to therapeutic and diagnostic applications.

Although 2'-O-alkylation of ribonucleosides with either the ligand itself or with a functional group amenable to indirect ligand attachment has often been employed in the synthesis of ribonucleoside 2'-conjugates, this method is generally limited by low yields and lack of regioselectivity. Attempts have been made to prepare aminooxy-modified oligonucleotide synthetic intermediates; see for example, U.S. Pat. No. 6,194,598, which reports the synthesis of 2'-O-aminooxyethyl derivatives. The 2'-O-aminooxyethyl derivatives, however, have certain drawbacks such as the protection offered by this derivative to 2'-OH group is more permanent than desirable.

The foregoing shows that there exists an unmet need for O-protected derivatives of nucleosides that are easy to prepare and that the protecting group is easily removed. There also exists an unmet need for a method of synthesis of oligonucleotides based on such O-protected derivatives.

BRIEF SUMMARY OF THE INVENTION

The invention provides a compound of the formula (I):

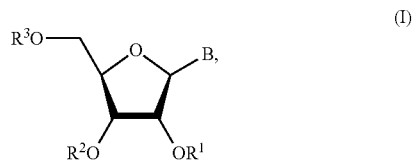

wherein B is an optionally protected nucleobase;
$R^1$, $R^2$, and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid or nucleotide moiety, a solid support, and a group of formula:

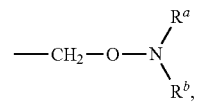

wherein $R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^b$ either independently or together with the N form an imide, imine, or a fragment of a functional group;
or $R^2$ and $R^3$ together form a hydroxyl protecting ring;
wherein at least one of $R^1$, $R^2$, and $R^3$ is

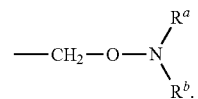

The compounds of formula (I) have one or more of the following advantageous features: (i) the O-protected compound, particularly the 2'-O-protected compound, is stable during the various reaction steps involved in oligonucleotide synthesis; the protecting group can be easily removed after the synthesis of the oligonucleotide, for example, by reaction with tetrabutylammonium fluoride; (ii) the O-protected groups, particularly the 2'-O-protected groups of the compound of formula (I) do not generate DNA/RNA alkylating side products, which have been reported during removal of 2'-O-(2-cyanoethyl)oxymethyl or 2'-O-[2-(4-tolylsulfonyl)ethoxymethyl groups under similar conditions; (iii) the ease of introduction of the O-protecting group to produce the compound of formula (I) according to a synthetic plan that is compatible with purine and pyrimidine ribonucleosides; (iv) the versatility of being useful for transiently or permanently labeling RNA and/or DNA sequences; and (v) permit the synthesis of native or modified RNA sequences with the flexibility of selecting various O-protecting or functional groups.

The invention also provides a method for preparing the compound of formula (I). The invention further provides a method for preparing an oligoribonucleotide of chain length n, where n is the number of nucleotide residues in the oligoribonucleotide, the method comprising step-wise addition of nucleotide residues to the 5'-terminus of a growing chain wherein the nucleotide residues are protected at the 2'-position with an aminooxymethyl protecting group.

The invention also provides a method for preparing an oligoribonucleotide of chain length n, where n is the number of nucleotide residues in the oligoribonucleotide, the method comprising:

(i) providing a substrate comprising a nucleoside protected at one of the 2'-, 3'-, or 5'-hydroxy function with an aminooxymethyl-derived protecting group and a solid support covalently linked to one of the remaining hydroxy functions, said substrate having the formula (XI):

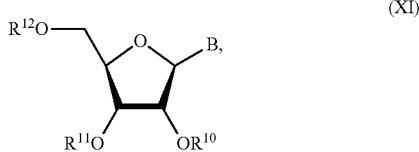

wherein B is an optionally protected nucleobase;
wherein at least one of $R^{10}$ and $R^{11}$ is an aminooxymethyl-derived protecting group and the other of $R^{10}$ and $R^{11}$ is a solid support, optionally linked to the oxygen atom through a carbonyl (>C=O) group; and $R^{12}$ is H;

(ii) providing a 5'-OH-protected nucleoside phosphoramidite derivative of formula (XII):

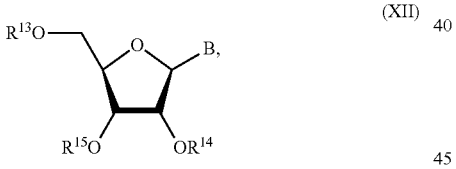

wherein:
$R^{13}$ is a hydroxyl protecting group;
$R^{14}$ is an aminooxymethyl-derived protecting group of the formula —CH$_2$—O—N=CHR$^{16}$ and $R^{15}$ is a phosphoramidite group, if $R^{10}$ of the substrate of formula (XI) is an aminooxymethyl-derived protecting group and $R^{11}$ is a solid support, optionally linked through a carbonyl (>C=O) group; or $R^{15}$ is an aminooxymethyl-derived protecting group of the formula —CH$_2$—O—N=CHR$^{16}$ and $R^{14}$ is a phosphoramidite group, if $R^{11}$ of the substrate of formula (XI) is an aminooxymethyl-derived protecting group and $R^{10}$ is a solid support, optionally linked through a carbonyl (>C=O) group;

wherein $R^{16}$ is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyanohaloalkyl, alkoxyhaloalkyl, aryloxyhaloalkyl, alkylthiohaloalkyl, arylthiohaloalkyl, alkylsulfinylhaloalkyl, arylsulfinylhaloalkyl, alkylsulfonylhaloalkyl and arylsulfonylhaloalkyl;

wherein the phosphoramidite group of $R^{14}$ or $R^{15}$ is of the formula: —P(R$^{17}$)(OR$^{18}$), wherein $R^{17}$ is an N,N-dialkylamino group or a saturated heterocyclic group having at least one nitrogen atom, optionally with one or more heteroatoms selected from the group consisting of O and S; and OR$^{18}$ is a phosphorus protecting group;

(iii) coupling the derivative of formula (XII) with the substrate of formula (XI) to obtain a product comprising the substrate coupled to the derivative of formula (XII);

(iv) 5'-capping of unreacted substrate of formula (XI) from step (iii);

(v) oxidizing the phosphite triester function present in the product of step (iii) to obtain a product having a protected phosphate triester function;

(vi) deprotecting the 5'-hydroxy group of the product of step (v);

(vii) repeating steps (iii)-(vi) n−1 times to build a protected oligonucleotide chain containing "n" nucleotide residues on the solid support;

(viii) removing the nucleobase and phosphate protecting groups and cleaving the oligonucleotide from the solid support; and (ix) optionally deprotecting the 2'-OH group or the 3'-OH group.

In an embodiment, the present further invention provides a method for preparing an oligoribonucleotide of chain length n, where n is the number of nucleotide residues in the oligoribonucleotide, the method comprising:

(i) providing a substrate comprising a nucleoside protected at the 2'-hydroxy function with an aminooxymethyl-derived protecting group and a solid support covalently linked to its 3'-hydroxy function, said substrate having the formula (IX):

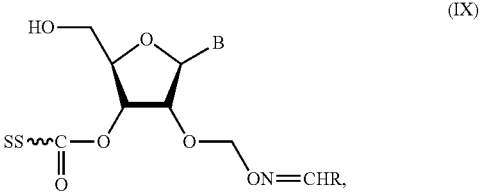

wherein B is an optionally protected nucleobase;
R is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyanohaloalkyl, alkoxyhaloalkyl, aryloxyhaloalkyl, alkylthiohaloalkyl, arylthiohaloalkyl, alkylsulfinylhaloalkyl, arylsulfinylhaloalkyl, alkylsulfonylhaloalkyl and arylsulfonylhaloalkyl;

and SS is a solid support;

(ii) providing a 5'-OH-protected nucleoside phosphoramidite derivative of formula (X):

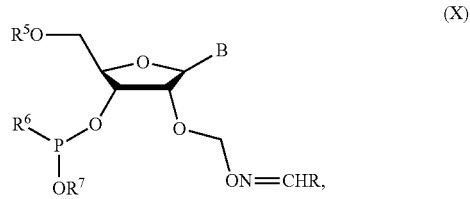

wherein $R^5$ is a hydroxyl protecting group; $R^6$ is a N,N-dialkylamino or saturated heterocyclic group having at least one nitrogen atom, optionally with one or more heteroatoms selected from the group consisting of O and S; $OR^7$ is a phosphorus protecting group;

(iii) coupling the derivative of formula (X) with the substrate of formula (IX) to obtain a product comprising the substrate coupled to the derivative of formula (X);

(iv) 5'-capping of any unreacted substrate of formula (IX) from step (iii);

(v) oxidizing the phosphite triester function present in the product of step (iii) to obtain a substrate having a protected phosphate triester function;

(vi) deprotecting the 5'-hydroxy group of the product of step (v);

(vii) repeating steps (iii)-(vi) n−1 times to build a protected oligonucleotide chain containing "n" nucleotide residues on the solid support;

(viii) removing the nucleobase and phosphate protecting groups and cleaving the oligonucleotide from the solid support; and (ix) optionally deprotecting the 2'-OH group.

The present invention also provides a method of preparing a compound of formula II:

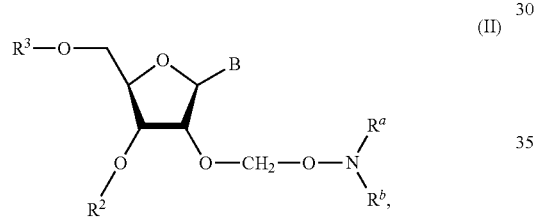

(II)

wherein B is an optionally protected nucleobase;

$R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^a$ either independently or together with the N form an imide, imine, or a fragment of a functional group; and $R^2$ and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, and a solid support;

the method comprising:

(i) converting the 2'-OH group to a 2'-methylthiomethoxy group of the compound of formula (III)

(III)

to obtain a compound of formula (IV):

(IV)

(ii) converting the 2-methylthiomethoxy group to a 2'-chloromethoxy group to obtain a compound of formula (V):

(V)

(iii) converting the 2'-chloromethoxy group of the compound of formula (V) to obtain a compound of the formula (VI);

(VI)

wherein R' is H or a substituent selected from the group consisting of halo, hydroxy, cyano, formyl, acyl, alkyl carbonyl, carboxyl, phosphoryl, phosphonyl, phosphono $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, guanidine, aldehydro, ureido, aminocarbonyl, $C_1$-$C_6$ alkyl, halo $C_1$-$C_6$ alkyl, hydroxy $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_6$-$C_{14}$ aryl, and $C_6$-$C_{14}$ aryl $C_1$-$C_6$ alkyl; and m is 1 to 4;

(iv) reacting the compound of formula (VI) with ammonium fluoride to obtain a compound of formula VII, in situ,

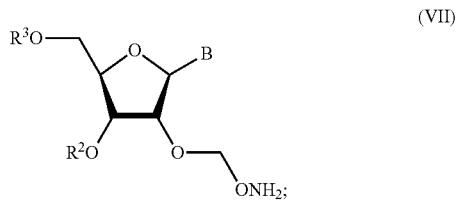

(VII)

and (v) reacting the compound of formula VII with a compound having aldehyde or ketone group to obtain a compound of formula (II).

BRIEF DESCRIPTION OF THE SEVERAL VIEWS OF THE DRAWINGS

FIG. 4 depicts the RP-HPLC analysis of the fluoride-assisted conversion of silica gel-purified 2'-O-(pyren–1-yl-methanimine-N-oxymethyl)uridine (6a) to uridine, where the X-axis is the retention time in minutes and the Y-axis is the intensity in arbitrary units (AU). FIG. 4A depicts the chromatogram of the silica gel purified 6a. FIG. 4B depicts the chromatogram of the conversion of 6a to uridine (peak at about 10 minutes retention time) by treatment with 0.5 M tetra-n-butylammonium fluoride in THF for 3 h at 55° C. FIG. 4C depicts the chromatogram of mixed uridine and pyrene-1-carbonitrile (17) commercial samples. Conditions for this Figure as well as FIGS. 5-9: RP-HPLC analysis was performed using UV detection (254 nm) and a 5 μm Supelcosil LC-18S column (25 cm×4.6 mm) according to the following conditions: starting from 0.1 M triethylammonium acetate pH 7.0, a linear gradient of 1% MeCN/min was pumped at a flow rate of 1 mL/min for 40 min; the gradient was then increased to 6% MeCN/min for 10 min at the same flow rate and kept isocratic for an additional 15 min. Peak heights are normalized to the highest peak, which is set to 1 arbitrary unit.

FIG. 5 depicts the RP-HPLC analysis of the fluoride-assisted conversion of the silica gel-purified biotinylated conjugate 10 to uridine.

FIG. 6 depicts the RP-HPLC analysis of the fluoride-assisted conversion of the silica gel-purified dansylated uridine conjugate 12 to uridine.

FIG. 7 depicts the RP-HPLC analysis of the fluoride-assisted conversion of the silica gel-purified dansylated uridine conjugate 14 to uridine. FIG. 7A depicts the chromatogram of the silica gel purified conjugate 14. FIG. 7B depicts the chromatogram of the conversion of 14 to uridine by treatment with 0.5 M tetra-n-butylammonium fluoride in THF for 48 h at 55° C. FIG. 7C depicts the chromatogram of a commercial sample of uridine co-mixed with an analytical sample of N-(4-cyanobut-1-yl)-5-(dimethylamino)naphthalene-1-sulfonamide (18).

FIG. 8 depicts the RP-HPLC analysis of the fluoride-assisted conversion of the silica gel-purified dansylated uridine conjugate 19 to uridine.

FIG. 9 depicts the RP-HPLC analysis of the fluoride-assisted conversion of the silica gel-purified dabsylated uridine conjugate 16 to uridine.

FIG. 13 compares the RP-HPLC analysis of r(Up)$_{20}$dT prepared from either ribonucleoside phosphoramidite 22a (R=$CH_2S(O)CH_3$) or commercial 2'-O-TBDMS ribonucleoside phosphoramidites, where the X-axis is the retention time in minutes and the Y-axis is the intensity in arbitrary units (AU).

DETAILED DESCRIPTION OF THE INVENTION

Figure 1:
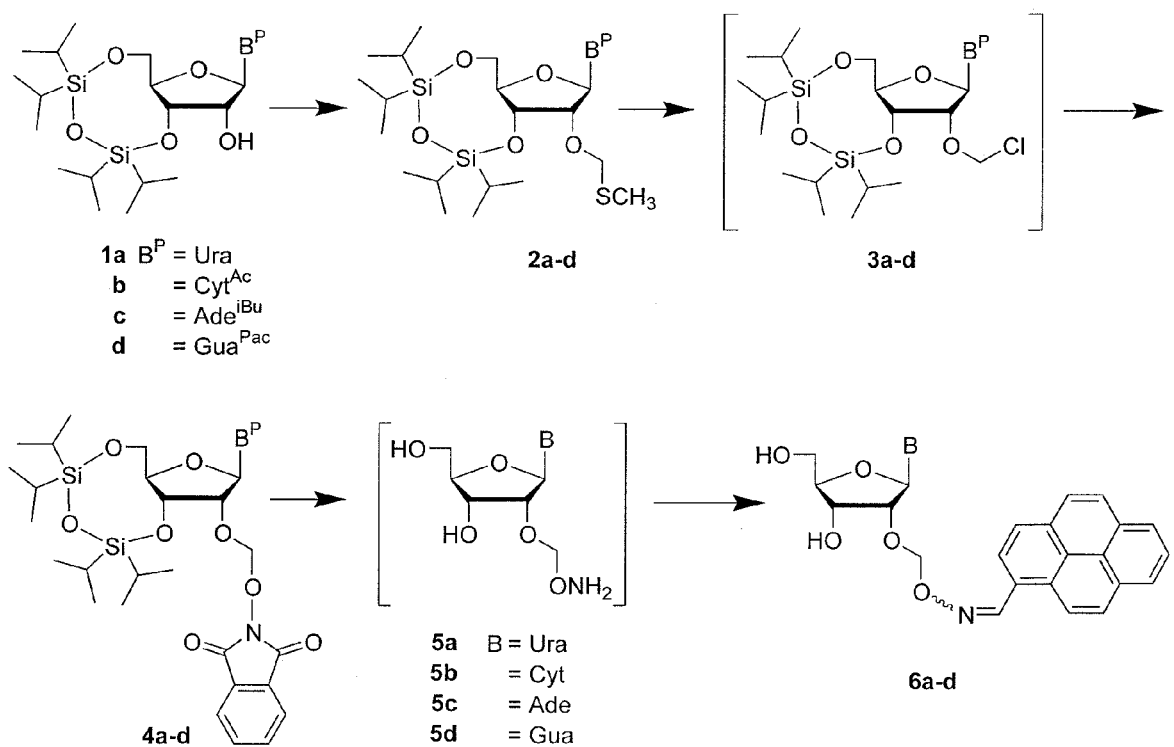
FIG. 1 depicts a schematic for the preparation of intermediates 2a-2d, 3a-3d, 4a-4-d, and 5a-5d and compounds 6a-6d of formula (I) in accordance with an embodiment of the invention. Compounds 1a-1d are commercially available.

In accordance with an embodiment, the invention provides an O-protected compound of the formula (I):

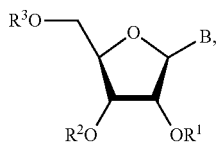

(I)

wherein B is an optionally protected nucleobase;

$R^1$, $R^2$, and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, a solid support, and a group of formula:

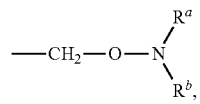

wherein $R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^b$ either independently or together with the N form an imide, imine, or a fragment of a functional group;

or $R^2$ and $R^3$ together form a hydroxyl protecting ring;

wherein at least one of $R^1$, $R^2$, and $R^3$ is

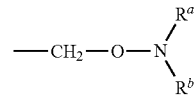

In accordance with the invention, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein n=1, 2, or 3.

In accordance with an embodiment, the alkyl group can be a $C_1$-$C_{12}$ alkyl, preferably a $C_1$-$C_6$ alkyl. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs such as in hydroxyalkyl, monohalo alkyl, dihalo alkyl, and trihalo alkyl. In accordance with an embodiment, the alkenyl group is preferably a $C_2$-$C_{12}$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. In accordance with an embodiment, the alkoxy group is preferably a $C_1$-$C_{12}$ alkoxy. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. The term "halo" refers to a halogen selected from the group consisting of fluorine, chlorine, bromine, and iodine, preferably fluorine.

In accordance with the invention, the term "heteroaryl" refers to a cyclic aromatic radical having from five to ten ring atoms of which at least one atom is O, S, or N, and the remaining atoms are carbon. Examples of heteroaryl radicals include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl. Examples of heterocyclyl groups include pyridyl, piperidinyl, piperazinyl, pyrazinyl, pyrrolyl, pyranyl, tetrahydropyranyl, tetrahydrothiopyranyl, pyrrolidinyl, furanyl, tetrahydrofuranyl, thiophenyl, tetrahydrothiopheneyl, purinyl, pyrimidinyl, thiazolyl, thiazolidinyl, thiazolinyl, oxazolyl, triazolyl, tetrazolyl, tetrazinyl, benzoxazolyl, morpholinyl, thiomorpholinyl, quinolinyl, and isoquinolinyl.

Any of the groups comprising alkyl can be linear or branched. When an aryl group is substituted with a substituent, e.g., halo, amino, alkyl, hydroxyl, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In accordance with an embodiment, the nucleobase or protected nucleobase can be any suitable nucleobase, for example, the nucleobase will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified. Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Examples of analogs include, but are not limited to, a nucleobase selected from the group consisting of cytosine, adenine, guanine, uracil, thymine, xanthine, hypoxanthine, alkyl derivatives thereof, amino derivatives thereof, halo derivatives thereof, and the like. In embodiments, examples of nucleobases or protected nucleobases include 2- r 8-aminoadenine, 2- or 8-alkyladenine, 5-halouracil, 5-halocytosine, 2,6-diaminopurine, 6-azauracil, 4-thiouracil, 5-trifluoromethyluracil, 5-(trifluoromethyl)cytosine, 6-aza thymine, 6-thioguanine, 7-deazaadenine, 7-deazaguanine, 8-mercaptoadenine, 8-alkylthioadenine, 8-hydroxyl/oxoadenine, 8-mercaptoguanine, 8 -alkylthioguanine, and 8-hydroxyl/oxoguanine Additional examples of nucleobases or protected nucleobases include 1-methyladenine, 2-methyladenine, $N^6$-methyladenine, $N^6$-isopentyladenine, 2-methylthio-$N^6$-isopentyladenine, $N^6,N^6$-dimethyladenine, 8-bromoadenine, 2-thiocytosine, 3-methylcytosine, 5-methylcytosine, 5-ethylcytosine, $N^4$-acetylcytosine, 1-methylguanine, $N^2$-methylguanine, 7-methylguanine, $N^2,N^2$-dimethylguanine, 8-bromoguanine, 8-chloroguanine, 8-aminoguanine, 8-methylguanine, 5-bromouracil, 5-chlorouracil, 5-iodouracil, 5-ethyluracil, 5-propyluracil, 5-methoxyuracil, 5-hydroxymethyluracil, 5-(carboxymethyl)uracil, 5-(methylaminomethyl)uracil, 5-(carboxymethylaminomethyl)uracil, 2-thiouracil, 5-methyl-2-thiouracil, 5-(2-bromovinyl)uracil, uracil-5-oxyacetic acid, uracil-5-oxyacetic acid methyl ester, 6-hydroxyaminopurine, and 6-thiopurine.

In accordance with embodiments of the invention, the optionally protected nucleobase is a nucleobase whose exocyclic amino group is protected by a labile protecting group, acid or base labile groups as appropriate. Examples of protecting groups include, for example, amides (e.g., trifluoroacetyl, acetyl, phenoxyacetyl, tert-butylphenoxyacetyl, benzoyl, and isobutyryl amides), carbamates (e.g., tert-butyloxycarbonyl, (4-nitrophenyl)ethyloxycarbonyl, and N-benzyloxycarbonyl), trityl, amidines and the like. These are defined in the literature: see, e.g., Iyer, *Current Protocols in Nucleic Acid Chemistry*, Vol. 1 (Beaucage S. L., Bergstrom, D. E., Glick, G. D. Jones R. A. eds); John Wiley and Sons: New York, 2000, pp. 2.1.1-2.1.17; Beaucage, et al., *Tetrahedron*, 48, 2223-2311 (1992); and McBride et al., *J. Am. Chem. Soc.*, 108, 2040-2048 (1986).

In accordance with embodiments, at least one or two of $R^1$, $R^2$, and $R^3$ can be

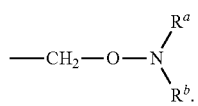

In accordance with any of the embodiments, in the compound of formula (I), $R^1$ is

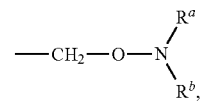

wherein $R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^a$ either independently or together with the N form an imide, imine, or a fragment of a functional group; and $R^2$ and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, and a solid support; or $R^2$ and $R^3$ together form a hydroxyl protecting ring.

In accordance with an embodiment, $R^a$ and $R^b$ together form an imide.

In accordance with an embodiment, $R^a$ and $R^b$ together form an imide group, for example, an imide group of the formula (Ia)

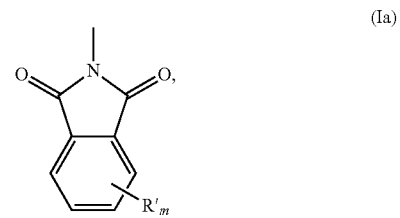

(Ia)

wherein R' is H or a substituent selected from the group consisting of halo, hydroxy, cyano, formyl, acyl, alkyl carbonyl, carboxyl, phosphoryl, phosphonyl, phosphono $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, guanidine, aldehydro, ureido, aminocarbonyl, $C_1$-$C_6$ alkyl, halo $C_1$-$C_6$ alkyl, hydroxy $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_6$-$C_{14}$ aryl, and $C_6$-$C_{14}$ aryl $C_1$-$C_6$ alkyl; and m is 1 to 4. In a preferred embodiment, R' is H.

In accordance with an embodiment, the invention provides a compound of formula (I), wherein $R^a$ and $R^b$ form a fragment of a functional group, which could be, for example, =CHR, wherein R is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyanohaloalkyl, alkoxyhaloalkyl, aryloxyhaloalkyl, alkylthiohaloalkyl, arylthiohaloalkyl, alkylsulfinylhaloalkyl, arylsulfinylhaloalkyl, alkylsulfonylhaloalkyl and arylsulfonylhaloalkyl. Particular examples of R include H, —$CH_3$, —$CH_2F$, —$CH_2Cl$, —$CH_2Br$, —$CH_2CN$, —$CH_2OCH_3$, —$CH_2SCH_3$, —$CH_2S(O)CH_3$, —$CH_2SO_2CH_3$, —$CH(CH_3)F$, —$CH(CH_3)CN$, —$CH(CH_3)OCH_3$, —$CH(CH_3)SCH_3$, —CH (CH₃)S(O)CH₃, —CH(CH₃)SO₂CH₃, —C(CH₃)₂Cl, —C(CH₃)₂Br, —CY(Z)F, —CY(Z)CN, —CY(Z)OCH₃, —CY(Z)SCH₃, —CY(Z)S(O)CH₃, or —CY(Z)SO₂CH₃, where Y is F or CH₃ and Z is F or CH₃.

In accordance with an embodiment of the invention, the functional group of the compound of formula (I) is selected from the group consisting of fluorescent labels, reporter groups, lipophilic groups, hydrophilic groups, cross-linking groups, surface active groups, affinity ligands, carbohydrates, steroids, amino acids, peptides, proteins, and metal complexes.

In accordance with an embodiment, the

moiety in formula (I) is an imine moiety of one of the following formulas:

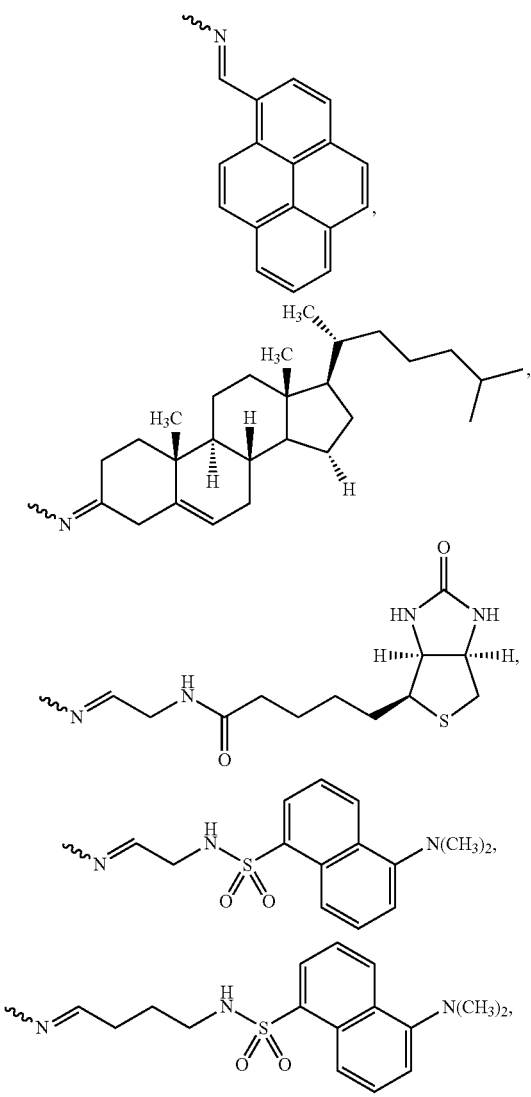

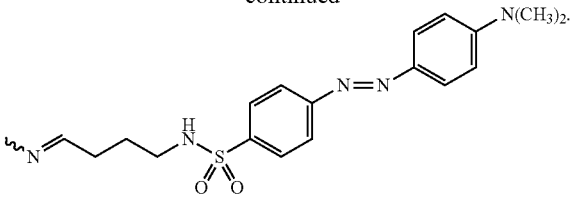

In accordance with an embodiment, any suitable hydroxyl protecting group can be used, for example, the hydroxyl protecting group is a silyl ether groups, e.g., trimethylsilyl, triethylsilyl, tert-butyldimethylsilyl, tert-butyldiphenylsilyl, dimethylphenylsilyl, and diphenylmethylsilyl; benzyl carbonates, trityl group, monomethoxytrityl, and dimethoxytrityl; esters, for example, acetate, benzoate, and the like; pixyl; tert-butyloxycarbonyl, 9-fluorenylmethoxycarbonyl (Fmoc), a tetrahydropyranyl group, and photolabile protecting groups, particularly, pixyl, acetyl, 9-fluorenylmethyloxycarbonyl (Fmoc), t-butyldimethylsilyl (TBDMS), trityl, monomethoxytrityl ("MMT" or "MMTr"), dimethoxytrityl ("DMT" or "DMTr").

In an embodiment, $R^2$ and $R^3$ together form a hydroxyl protecting group or ring, for example, where the hydroxyl protecting group or ring is of the formula protecting two hydroxyl groups simultaneously:

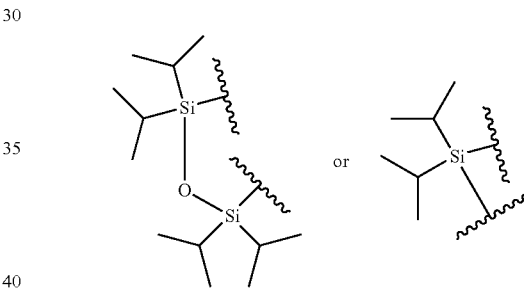

In accordance with an embodiment, $R^3$ is a solid support. Any suitable solid support can be used in accordance with the present invention. Solid supports are commonly known in the art and include, for example, organic solid supports (e.g., crosslinked polystyrene), inorganic solid supports (e.g., silica supports), and like. Preferably, the solid support is an inorganic support, which is more preferably a silica support. It will be appreciated that the solid support can include linkers, spacers, arms, and other moieties (organic and inorganic moieties) known in the art for manipulating attachment to a solid support. It will also be appreciated that the solid support can be bonded to the molecule directly, without the use of linkers, spacers, arms, or other connecting moieties; see, e.g. Beaucage et al., *Tetrahedron*, 49, 6123-6194 (1993). In a particular embodiment, the solid support is a controlled pore glass support.

In an embodiment, $R^3$ is dimethoxytrityl. In another embodiment, $R^2$ and $R^3$ are H. In a further embodiment, $R^2$ and/or $R^3$ is a nucleotide moiety, e.g., an oligonucleotide linked through a phosphotriester, phosphodiester, phosphorothioate triester, phosphorothioate diester or a phosphoramidate linkage.

In accordance with an embodiment, the invention further provides a method of preparing a compound of formula II:

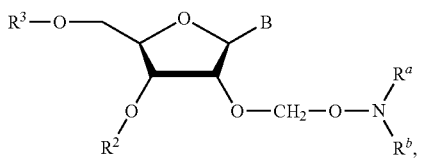

(II)

wherein B is an optionally protected nucleobase;

$R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^a$ either independently or together with the N form an imide, imine, or a fragment of a functional group; and $R^2$ and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, and a solid support;

the method comprising:

(i) converting the 2'-OH group to a 2'-methylthiomethoxy group of the compound of formula (III)

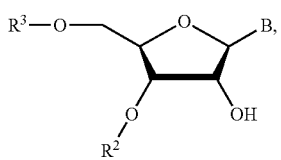

(III)

to obtain a compound of formula (IV):

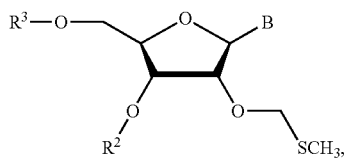

(IV)

(ii) converting the 2'-methylthiomethoxy group to a 2'-chloromethoxy group to obtain a compound of formula (V):

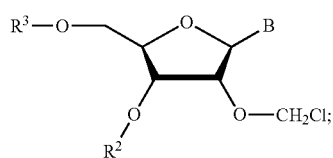

(V)

(iii) converting the 2'-chloromethoxy group of the compound of formula (V) to obtain a compound of the formula (VI);

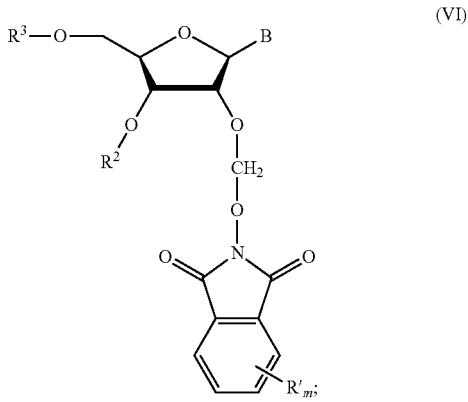

(VI)

wherein R' is H or a substituent selected from the group consisting of halo, hydroxy, cyano, formyl, acyl, alkyl carbonyl, carboxyl, phosphoryl, phosphonyl, phosphono $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, guanidine, aldehydro, ureido, aminocarbonyl, $C_1$-$C_6$ alkyl, halo $C_1$-$C_6$ alkyl, hydroxy $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_6$-$C_{14}$ aryl, and $C_6$-$C_{14}$ aryl $C_1$-$C_6$ alkyl; and m is 1 to 4;

(iv) reacting the compound of formula (VI) with ammonium fluoride to obtain a compound of formula VII, in situ,

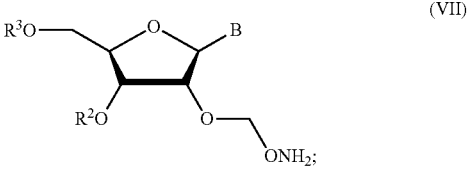

(VII)

and (v) reacting the compound of formula VII with a compound having aldehyde or ketone group to obtain a compound of formula (II).

In an embodiment, the above method can further include protecting the 5'-OH group of the compound of formula II where $R^3$=H, to obtain a 5'-OH protected compound. In accordance with an embodiment, the above method can further include coupling the 5'-OH protected compound to a solid support through the 3'-OH group followed by removing the protecting group at the 5'-position to obtain a compound of formula I linked to a solid support. In an embodiment, the above method further includes converting the 3'-OH group to a phosphoramidite ester.

FIG. 1 illustrates a method of preparing embodiment compounds of formula (I). Thus, for example, compounds 6a-d can be prepared starting from compounds Ia-d. The reaction of 1a-d with DMSO, acetic anhydride and acetic acid over a period of 16 h at ~50° C. gave, after purification by chromatography on silica gel, the ribonucleoside 2'-thioacetals 2a-d in isolated yields of 85 to 94%. The yields of 2a-d are somewhat dependent on the ratio of the reactants used in the thioacetalization of 1a-d; the ratios of DMSO, acetic anhydride and acetic acid, as reported by Semenyuk et al., *J. Am. Chem. Soc.* 2006, 128, 12356-12357, were implemented into the preparation of 2a-d, which were characterized by $^1$H and $^{13}$C NMR spectroscopies and by high resolution mass spectrometry (HRMS). Conversion of the methylhiomethyl ether functions of 2a-d to chloromethyl ether derivatives (3a-d) was effected by treatment with sulfuryl chloride in $CH_2Cl_2$; 3a-d were isolated as amorphous materials. The addition of a premixed solution of N-hydroxyphthalimide and a limiting amount of DBU (0.9 molar equiv) in $CH_2Cl_2$ to 3a-d produced the 2'-O-phthalimidooxymethyl ribonucleosides 4a-d in yields of 66% to 94% relative to the molar amounts of 2a-d that were used as starting materials. The silica gel-purified ribonucleosides 4a-d were characterized by $^1$H and $^{13}$C NMR spectroscopies and HRMS.

Desilylation of 4a-d was performed using a suspension of $NH_4F$ in methanol (Semenyuk et al., supra) over a period of 16 h at ~25° C. Unexpectedly, the phthalimido group was also cleaved under these conditions, affording the 2'-O-aminooxymethyl ribonucleosides 5a-d after N-deacylation of the nucleobases by exposure to conc. aqueous $NH_3$. After removal of excess $NH_3$, 5a-d were reacted with 1-pyrenecarboxaldehyde at 55° C. in MeOH to give the pyrenylated ribonucleoside conjugates 6a-d in yields of 69% to 82% relative to the molar amounts of 4a-d used as starting materials. The identities of 6a-d were confirmed by HRMS. As a general precautionary measure, it is preferable to perform N-deacylation of the nucleobases prior to any oximation reaction in order to prevent partial cleavage of oxime ethers, especially those with relatively acidic oximic protons, under basic conditions.

It is worth noting that when the desilylation of 4a was effected by treatment with 0.5 M TBAF in THF, uridine was the only nucleosidic product detected by reversed-phase high performance liquid chromatography (RP-HPLC) analysis of the deprotection reaction. Likewise, when 4a was successively treated with hydrazine hydrate, to release the aminooxymethyl function, and with $NH_4F$ in methanol to desilylate the 5'- and 3'-hydroxy groups, RP-HPLC analysis of the reaction revealed only uridine as the nucleosidic product. The identities of 5a-d were corroborated by HRMS and by $^1$H and $^{13}$C NMR analyses of silica-gel purified samples isolated from the $NH_4F$/MeOH deprotection of 4a-d.

Figure 2:
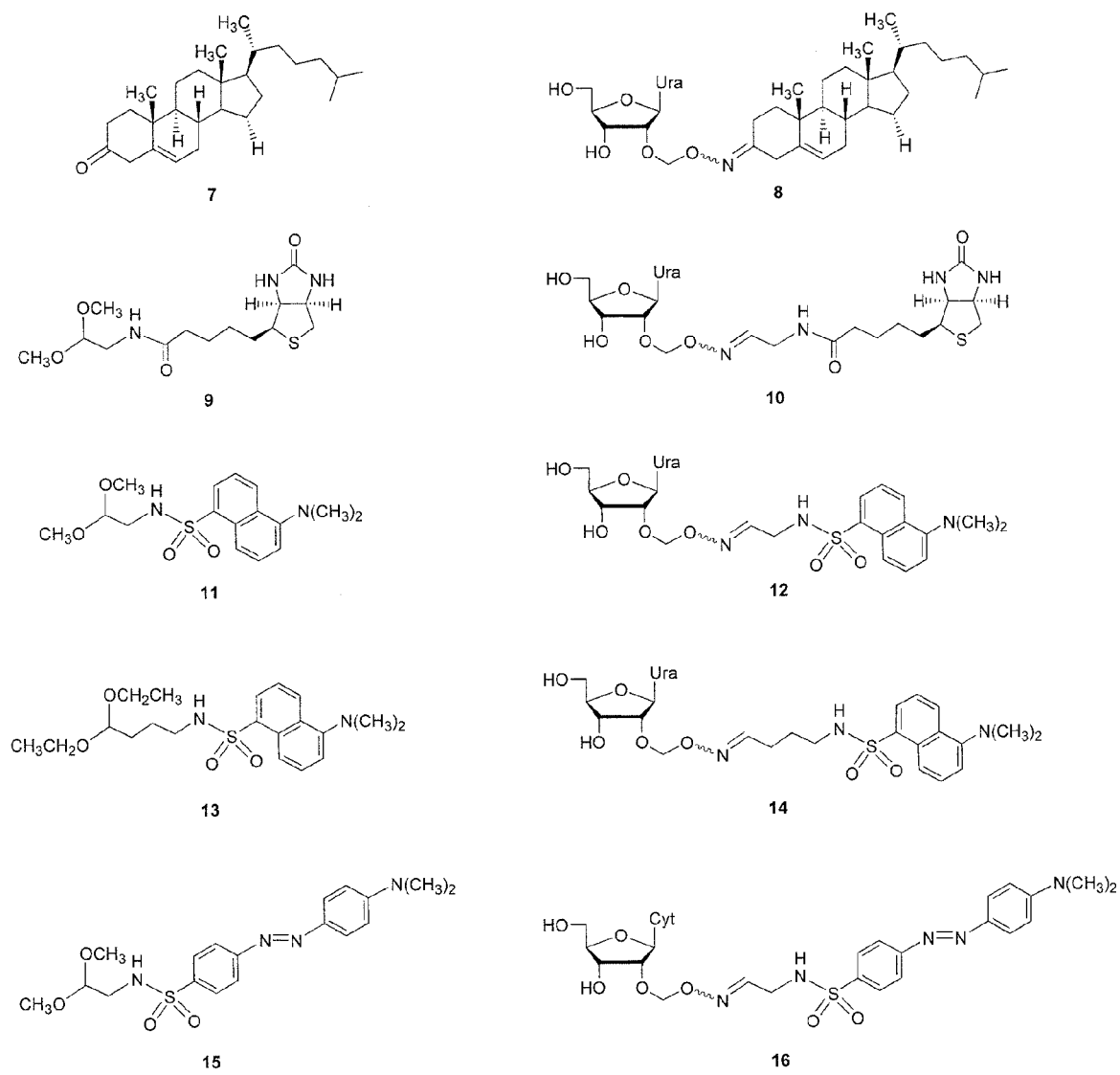
FIG. 2 depicts the structures of compounds 8, 10, 12, 14, and 16 in accordance with an embodiment of the invention and of compounds 7, 9, 11, 13, and 15 that were used to prepare compounds 8, 10, 12, 14, and 16, respectively.

In order to further demonstrate the versatility of 4a-d in the preparation of ribonucleoside 2'-conjugates (FIG. 2), the ribonucleoside 4a was converted to 2'-O-aminooxymethyl uridine (5a), as described above, by treatment with $NH_4F$/MeOH, and was reacted with cholesten-3-one (7) and aldehydes derived from N-(2,2-dimethoxyethyl)biotinamide (9), N-(2,2-dimethoxyethyl)-5-(dimethylamino)naphthalene-1-sulfonamide (11) and N-(4,4-diethoxybutyl)-5-(dimethylamino)naphthalene-1-sulfonamide (13) to produce the uridine 2'-conjugates 8, 10, 12 and 14, respectively. The reaction of 2'-O-aminooxymethyl cytidine (5b) with the aldehyde derived from N-(2,2-dimethoxyethyl)-4-(dimethylamino) azobenzene-4'-sulfonamide (15) gave the cytidine 2'-conjugate 16. The acetals 9, 11, 13 and 15 were conveniently prepared from the reaction of aminoacetaldehyde dimethyl acetal or 4-aminobutyraldehyde diethyl acetal with D-(+)-Biotin 2-nitrophenyl ester, dansyl chloride and dabsyl chloride in the presence of triethylamine. These acetals were isolated in yields of 91-95% and were characterized by $^1$H and $^{13}$C NMR spectroscopies and by HRMS. The equilibration between acetals 9, 11, and 13 and their corresponding aldehydes on exposure to coned HCl in MeOH led, after evaporation under reduced pressure and preferably after neutralization of residual acid with aq. $NaHCO_3$, to efficient conjugation with 2'-O-aminooxymethyl ribonucleosides. The acetal 15 did not significantly convert to the aldehyde when reacted with coned HCl; protonation of the azo function may have significantly decreased its solubility in MeOH. This shortcoming was avoided when the acetal 15 was treated with a solution of 10% iodine in acetone and further processed as described in the literature. Sun, J.; Dong, Y.; Cao, L.; Wang, X.; Wang, S.; Hu, Y. *J. Org. Chem.* 2004, 69, 8932-8934. The crude N-(2-oxoethyl)-4-(dimethylamino)azobenzene-4'-sulfonamide was isolated and without further purification, was reacted with the 2'-O-aminooxymethyl ribonucleoside 5b. The cytidine 2'-conjugate 16 was obtained in a yield of 61% and was characterized by HRMS and by $^1$H and $^{13}$C NMR spectroscopies.

Figure 3:
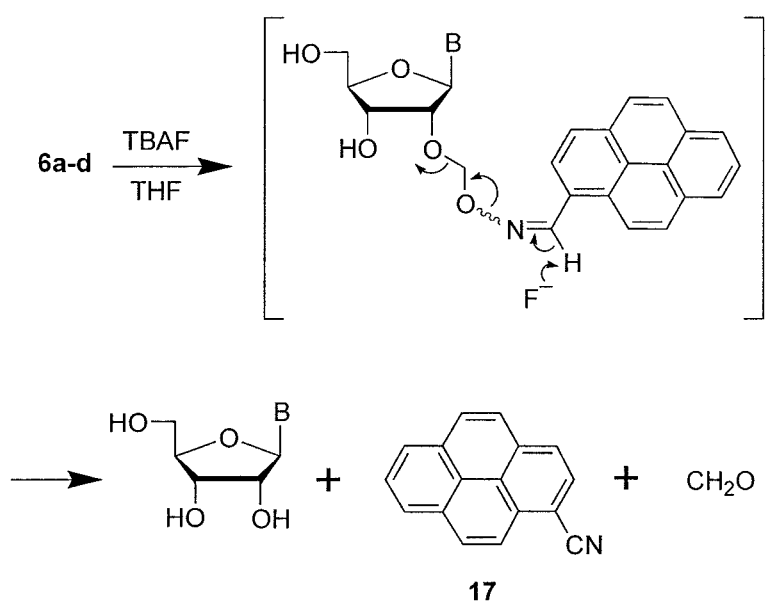
FIG. 3 illustrates the fluoride-assisted conversion of 2'-O-pyrenylated ribonucleosides (6a-d) in accordance with an embodiment of the invention to native ribonucleosides. TBAF: tetra-n-butylammonium fluoride; B: uracil-1-yl, cytosin–1-yl, adenin-9-yl, or guanin-9-yl.

Uridine and cytidine 2'-conjugates 6a-d, 10, 12, 14 and 16 are stable conjugates, which can be conveniently and efficiently converted to their native ribonucleosides upon treatment with 0.5 M TBAF in THF. A proposed mechanism for these transformations is shown in FIG. 3 and is supported by representative RP-HPLC profiles illustrating the conversion of 6a, 10 and 14 to uridine. The RP-HPLC chromatograms in FIG. 4 demonstrate the formation of pyrene-1-carbonitrile (17) and N-(4-cyanobut-1-yl)-5-(dimethylamino)naphthalene-1-sulfonamide (18) as side products from the fluoride-assisted cleavage of the 2'-iminooxymethyl ether function from 6a and 14, respectively.

Figures 4A, 4B, 4C:
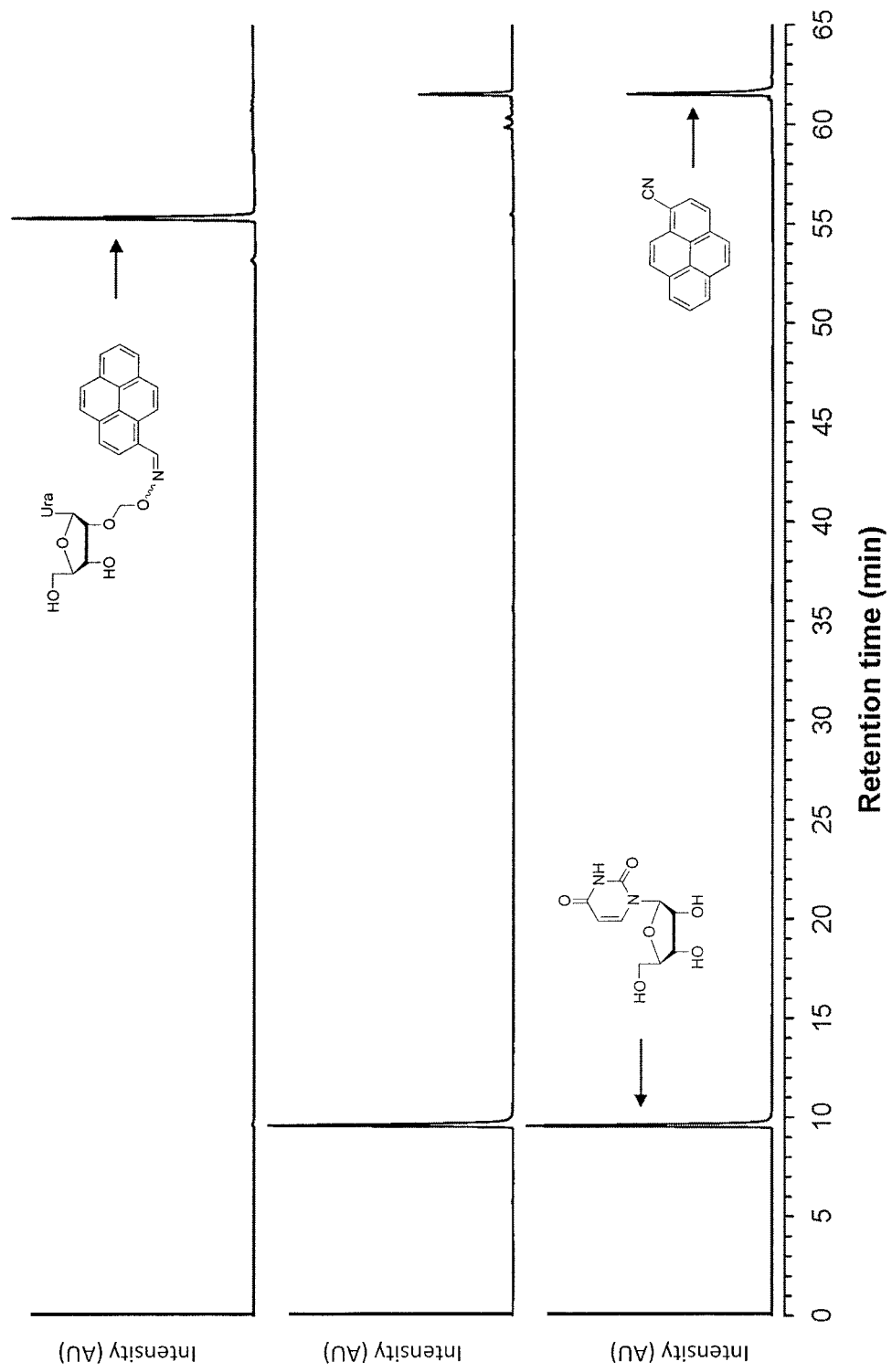
Figures 5A, 5B, 5C:
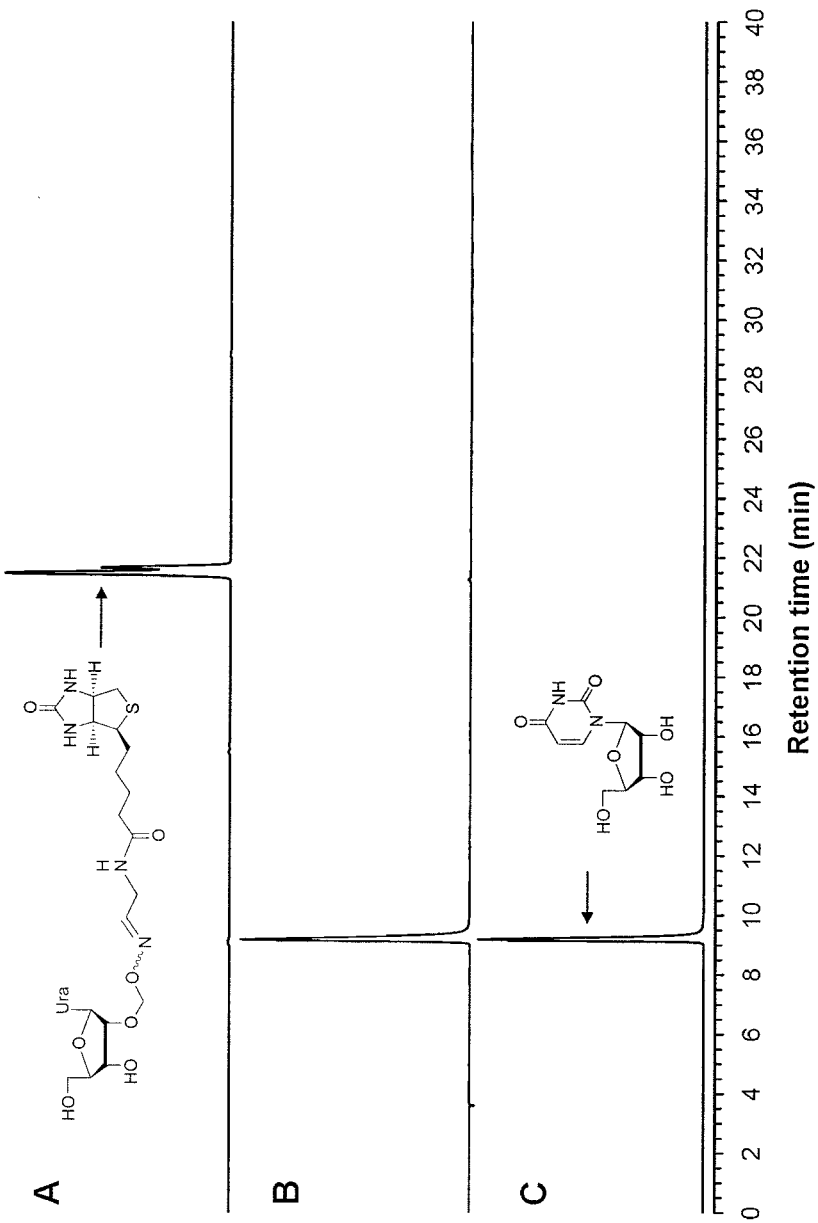
FIG. 5A depicts the chromatogram of the silica gel purified biotin-uridine conjugate 10.
FIG. 5B depicts the chromatogram of the conversion of 10 to uridine by treatment with 0.5 M tetra-n-butylammonium fluoride in THF for 6 h at 55° C.
FIG. 5C depicts the chromatogram of a commercial sample of uridine.
Figures 6A, 6B, 6C:
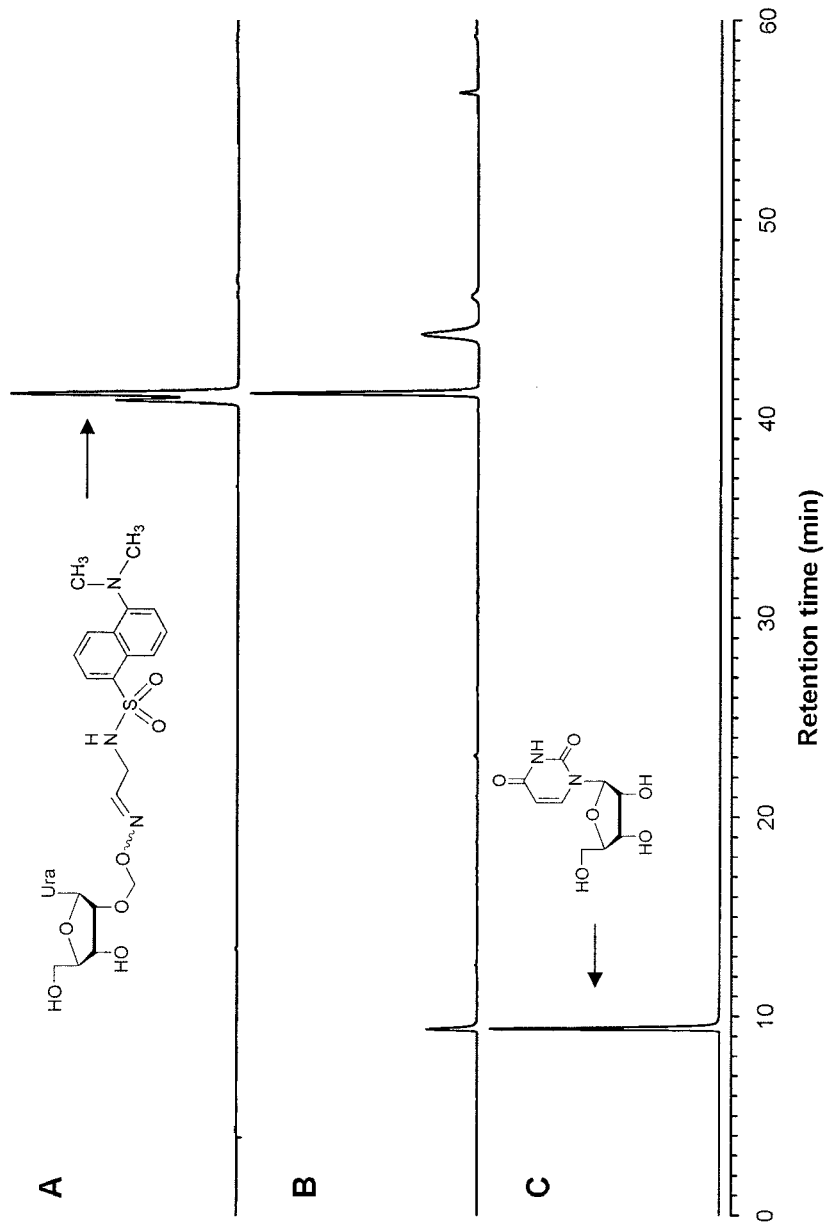
FIG. 6A depicts the chromatogram of the silica gel purified conjugate 12.
FIG. 6B depicts the chromatogram of the conversion of 12 to uridine by treatment with 0.5 M tetra-n-butylammonium fluoride in THF for 24 h at 55° C.
FIG. 6C depicts the chromatogram of a commercial sample of uridine.
Figures 8A, 8B:
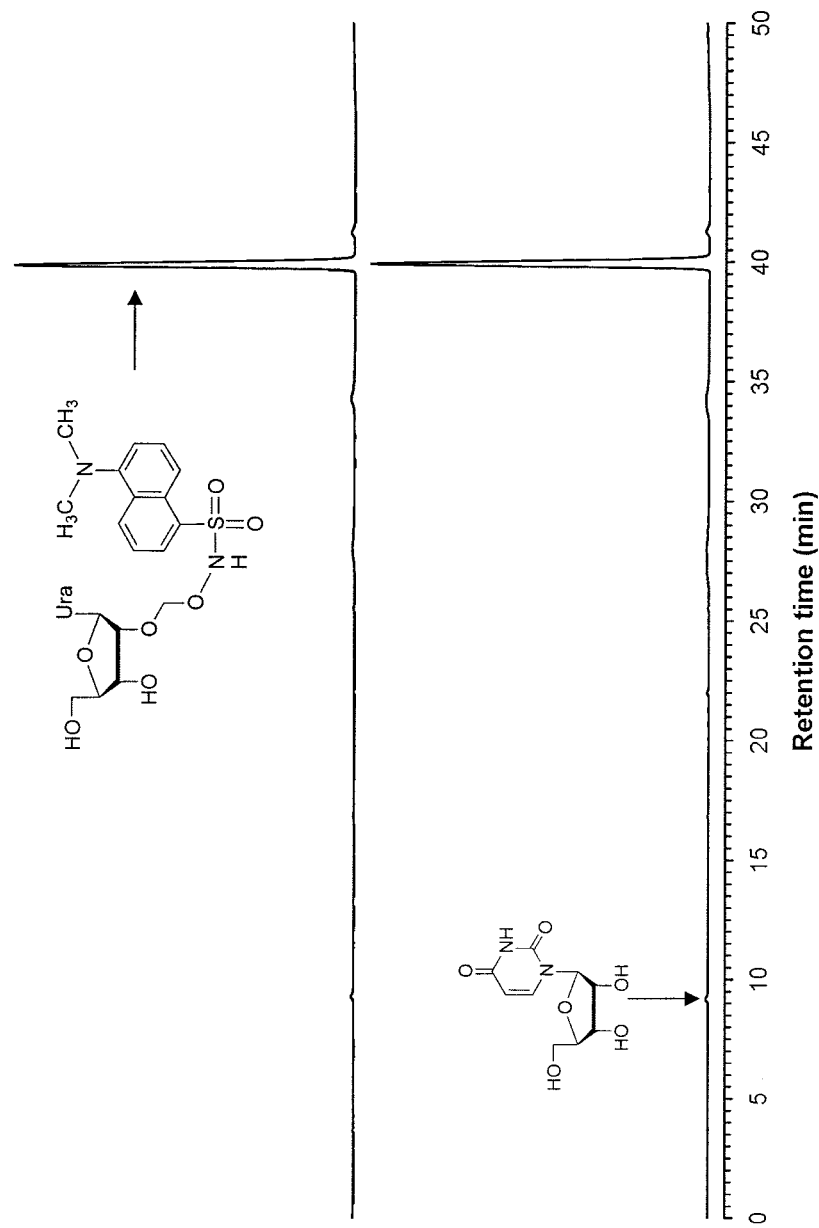
FIG. 8A depicts the chromatogram of the silica gel purified 19.
FIG. 8B depicts the chromatogram of the conversion of 19 to uridine by treatment with 0.5 M tetra-n-butylammonium fluoride in THF for 72 h at 55° C.
Figures 9A, 9B, 9C:
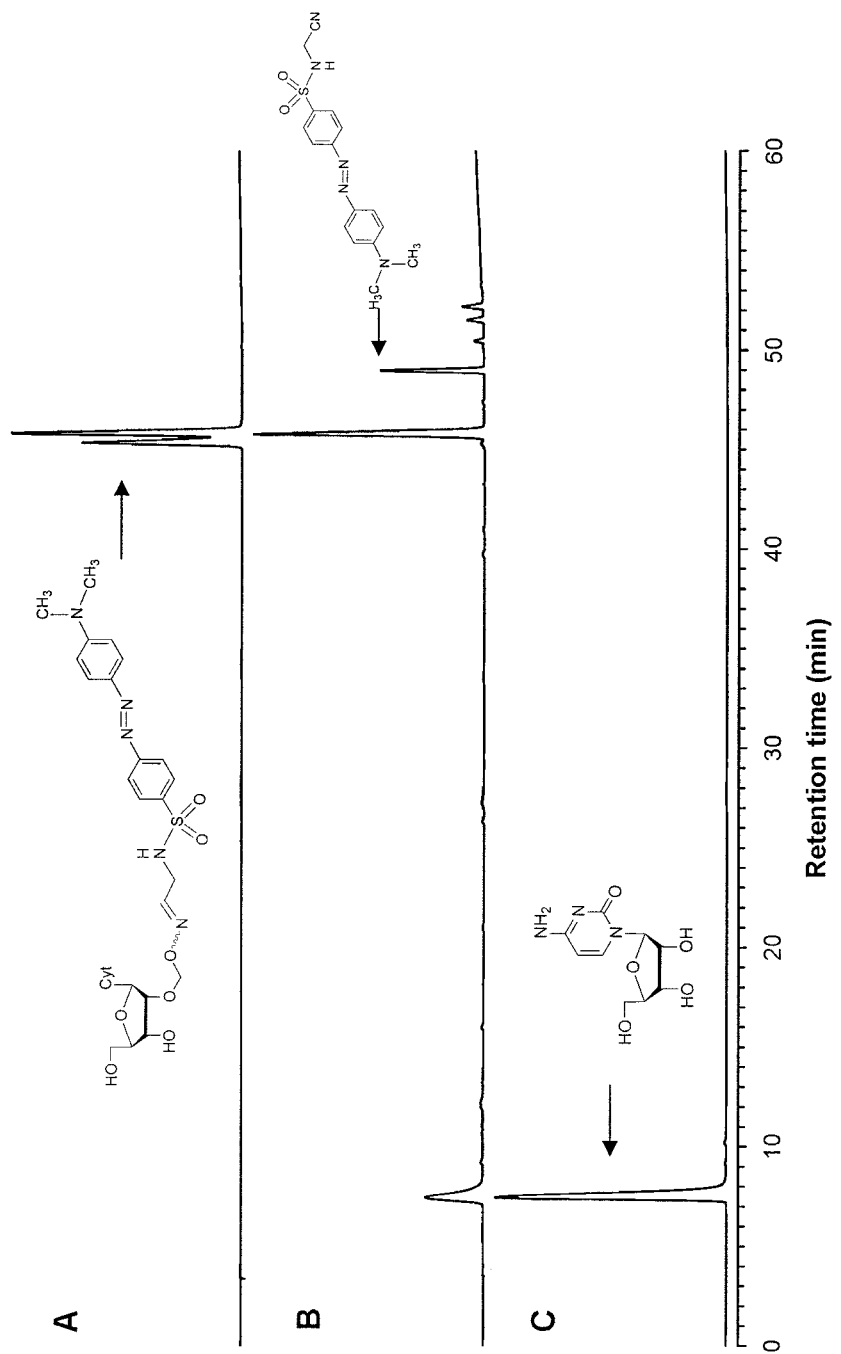
FIG. 9A depicts the chromatogram of the silica gel-purified 16.
FIG. 9B depicts the chromatogram of the conversion of 16 to cytidine by treatment with 0.5 M tetra-n-butylammonium fluoride in THF for 24 h at 55° C.
FIG. 9C depicts the chromatogram of a commercial sample of cytidine.

The identities of pyrene-1-carbonitrile and N-(4-cyanobut-1-yl)-5-(dimethylamino)naphthalene-1-sulfonamide were confirmed by RP-HPLC analyses of authentic samples, which revealed identical retention times ($t_R$=61.5 and 48.2 min, respectively, see FIGS. 4 and 7). Accordingly, the present invention provides in an embodiment a method for cleaving ribonucleoside 2'-aryl or -alkyliminooxy ethers through a fluoride-mediated reaction.

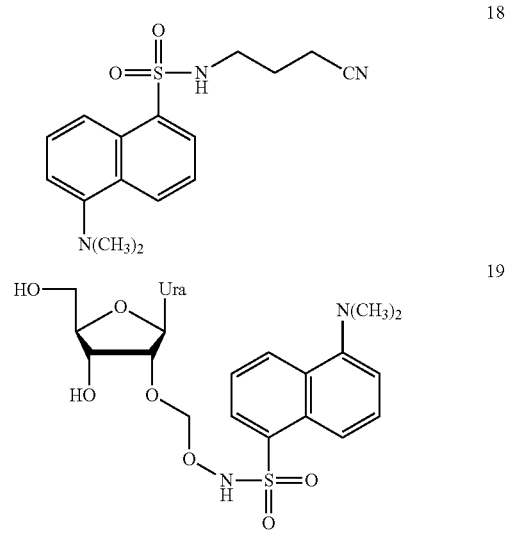

In contrast to the oximation of aldehydes with 5a, its reaction with cholesten-3-one (7) and dansyl chloride gave, as expected, the permanent uridine 2'-conjugates 8 and 19, respectively. These conjugates were both found stable to TBAF/THF under the conditions used for the conversion of 6a-d, 10, 12, 14, and 16 to uridine or cytidine. Indeed, treatment of 19 with 0.5 M TBAF in THF for 72 h at 55° C. produced uridine to the extent of less than 1%, as determined by RP-HPLC analysis of the reaction products.

The conjugates 6a-d, 10, 12, 14 and 16 exist as a mixture of E- and Z-geometrical isomers; one of these isomers appears to undergo fluoride-assisted cleavage of the 2'-iminooxymethyl ether function at a faster rate than the other geometrical isomer as judged by RP-HPLC analysis of the cleavage reactions. The proximity of an electron-donating function to the 2'-iminooxymethyl ether function clearly affects the rates of the fluoride-assisted cleavage reaction. While the fluoride-mediated conversion of 6a-d to uridine was complete within 4 h at 55° C., it took 6 h for 10 to convert to uridine under identical conditions.

Without wishing to be bound by any theory or mechanism, it is believed that in the presence of the fluoride ion, which is a strong base in aprotic solvent, the amide function of 10 ($pK_a$~25) may become ionized to some extent and decreases the acidity of the oximic proton, relative to that of 6a-d, as a consequence of the electron-donating properties of the ionized amide function; the reduced acidity of the oximic proton would then result in a slower β-elimination reaction. This belief is further supported by the considerably slower fluoride-assisted conversion of 12 to uridine, which was only 15% complete after 24 h at 55° C. The relatively acidic sulfonamide function of 12 ($pK_a$~10) is presumably ionized to a larger extent than that of an amide function by the strongly basic fluoride ion and further decreases the acidity of the oximic proton, thereby leading to slower β-elimination rates relative to those of 6a-d and 10 under identical conditions. Also consistent with this belief is that when the sulfonamide function is increasingly distal to the oximic proton, the electron-donating properties of the ionized sulfonamide have a lesser effect on the acidity of the oximic proton and result in relatively faster β-elimination rates. Typically, the fluoride-assisted conversion of 14 to uridine was complete within 48 h at 55° C.; this β-elimination rate is faster than that of 12 but still significantly slower than those of 6a-d and 10. Given the similarity of 16 and 12 in terms of the proximity of the sulfonamide function to the oximic proton, the conversion of 16 to cytidine by treatment with 0.5 M TBAF in THF was only 25% complete after 24 h at 55° C.

The present invention also provides a method for preparing an oligoribonucleotide of chain length n, where n is the number of nucleotide residues in the oligoribonucleotide, the method comprising step-wise addition of nucleotide residues to the 5'-terminus of a growing chain wherein the nucleotide residues are protected at the 2'-position with an aminooxymethyl-derived protecting group.

In a further embodiment, the invention provides a method for preparing an oligoribonucleotide of chain length n, where n is the number of nucleotide residues in the oligoribonucleotide, the method comprising:

(i) providing a substrate comprising a nucleoside protected at one of the 2'-, 3'-, or 5'-hydroxy function with an aminooxymethyl-derived protecting group and a solid support covalently linked to one of the remaining hydroxy functions, said substrate having the formula (XI):

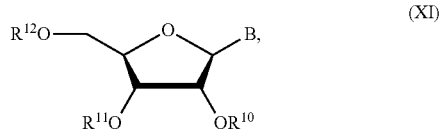

wherein B is an optionally protected nucleobase;
wherein at least one of $R^{10}$ and $R^{11}$ is an aminooxymethyl-derived protecting group and the other of $R^{10}$ and $R^{11}$ is a solid support, optionally linked to the oxygen atom through a carbonyl (>C=O) group; and $R^{12}$ is H;

(ii) providing a 5'-OH-protected nucleoside phosphoramidite derivative of formula (XII):

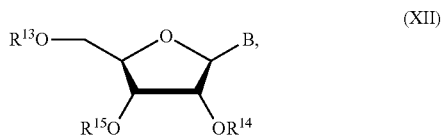

wherein:
$R^{13}$ is a hydroxyl protecting group;
$R^{14}$ is an aminooxymethyl-derived protecting group of the formula —$CH_2$—O—N=$CHR^{16}$ and $R^{15}$ is a phosphoramidite group, if $R^{10}$ of the substrate of formula (XI) is an aminooxymethyl-derived protecting group and $R^{11}$ is a solid support, optionally linked through a carbonyl (>C=O) group; or $R^{15}$ is an aminooxymethyl-derived protecting group of the formula —$CH_2$—O—N=$CHR^{16}$ and $R^{14}$ is a phosphoramidite group, if $R^{11}$ of the substrate of formula (XI) is an aminooxymethyl-derived protecting group and $R^{10}$ is a solid support, optionally linked through a carbonyl (>C=O) group;

wherein $R^{16}$ is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyanohaloalkyl, alkoxyhaloalkyl, aryloxyhaloalkyl, alkylthiohaloalkyl, arylthiohaloalkyl, alkylsulfinylhaloalkyl, arylsulfinylhaloalkyl, alkylsulfonylhaloalkyl and arylsulfonylhaloalkyl;

wherein the phosphoramidite group $R^{14}$ or $R^{15}$ is of the formula: —$P(R^{17})(OR^{18})$, wherein $R^{17}$ is an N,N-dialkylamino group or a saturated heterocyclic group having at least one nitrogen atom, optionally with one or more heteroatoms selected from the group consisting of O and S; and $OR^{18}$ is a phosphorus protecting group;

(iii) coupling the derivative of formula (XII) with the substrate of formula (XI) to obtain a product comprising the substrate coupled to the derivative of formula (XII);

(iv) 5'-capping of unreacted substrate of formula (XI) from step (iii);

(v) oxidizing the phosphite triester function present in the product of step (iii) to obtain a product having a protected phosphate triester function;

(vi) deprotecting the 5'-hydroxy group of the product of step (v);

(vii) repeating steps (iii)-(vi) n–1 times to build a protected oligonucleotide chain containing "n" nucleotide residues on the solid support;

(viii) removing the nucleobase and phosphate protecting groups and cleaving the oligonucleotide from the solid support; and (ix) optionally deprotecting the 2'-OH group or the 3'-OH group.

In accordance with a particular embodiment, the invention provides a method for preparing an oligoribonucleotide of chain length n, where n is the number of nucleotide residues in the oligoribonucleotide, the method comprising:

(i) providing a substrate comprising a nucleoside, the 2'-hydroxy function or which is protected with an aminooxymethyl-derived group, and a solid support covalently linked to the 3'-hydroxy function of the nucleoside, the substrate having the formula (IX):

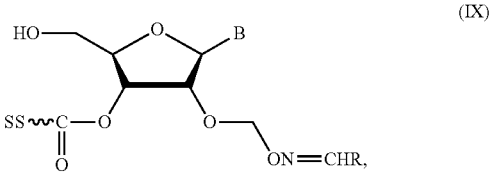

(IX)

wherein B is an optionally protected nucleobase;

R is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyanohaloalkyl, alkoxyhaloalkyl, aryloxyhaloalkyl, alkylthiohaloalkyl, arylthiohaloalkyl, alkylsulfinylhaloalkyl, arylsulfinylhaloalkyl, alkylsulfonylhaloalkyl and arylsulfonylhaloalkyl;

and SS is a solid support;

(ii) providing a 5'-OH-protected phosphoramidite derivative of a nucleoside of formula (X):

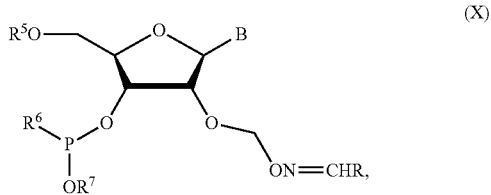

(X)

wherein $R^5$ is a hydroxyl protecting group; $R^6$ is an N,N-dialkylamino or saturated heterocyclic group having at least one nitrogen atom, optionally with one or more heteroatoms selected from the group consisting of O and S, for example, pyrrolidino, piperidino, morpholino or thiomorpholino group; $OR^7$ is a phosphorus protecting group;

(iii) coupling the derivative of formula (X) with the substrate of formula (IX) to obtain a product comprising the substrate coupled to the derivative of formula (X);

(iv) 5'-capping of unreacted substrate of formula (IX) from step (iii);

(v) oxidizing the phosphite triester function present in the product of step (iii) to obtain a product having a protected phosphate triester function;

(vi) deprotecting the 5'-hydroxy group of the product of step (v);

(vii) repeating steps (iii)-(vi) n−1 times to build a protected oligonucleotide of chain length n on the solid support;

(viii) removing the nucleobase and phosphate protecting groups and cleaving the oligonucleotide from the solid support; and (ix) optionally deprotecting the 2'-OH group.

In the above embodiments of the invention, n can be 2 to 200, preferably 5 to 100, and more preferably 10 to 30. Particular embodiments include n=10, 20, 30, 40, 50, 60, and higher.

In accordance with an embodiment of the invention, the tricoordinated phosphorus protecting groups $R^6$ is selected from the group consisting of an N,N-dialkylamino group or a saturated heterocyclic group having at least one nitrogen atom, optionally with one or more heteroatoms selected from the group consisting of O and S, and $OR^7$ is selected from the group consisting of alkoxy, alkenyloxy, e.g., allyloxy, cyanoalkoxy, trialkylsilylalkoxy, methylsulfonylalkoxy and arylsulfonylalkoxy, e.g., as described in the literature (Beaucage, et al., *Tetrahedron*, 48, 2223-2311 (1992)). Similar definitions apply to $R^{17}$ and $OR^{18}$.

Oxidizing agents that can be used in accordance with the present invention include any suitable reagent that can oxidize a tricoordinated phosphorus atom, particularly a phosphite, to provide a phosphorus atom having a valence of greater than three, preferably a tetracoordinated phosphorus atom such as, for example, a phosphate, or an equivalent thereof. Suitable oxidizing agents include, for example, $I_2/H_2O$, peroxides, such as tert-butyl hydrogen peroxide, and the like.

Sulfurizing agents that can be used in accordance with the present invention include any suitable reagent that can sulfurize a tricoordinated phosphorus atom, particularly a phosphite, to provide a phosphorus atom with a valence of greater than three, preferably a tetracoordinated phosphorus atom such as, for example, a phosphorothioate, or an equivalent thereof. Suitable sulfurizing agents include, for example, 3H-1,2-benzodithiol-3-one-1,1-dioxide ("Beaucage Reagent"), phenylacetyl disulfide, bis(O,O-diisopropoxyphosphinothioyl) disulfide, N-formamidino-3H-1,2,4-dithiazole-3-thione, and the like.

Selenizing agents that can be used in accordance with the present invention include any suitable reagent that can selenize a tricoordinated phosphorus atom, particularly a phosphite, to provide a phosphorus atom having a valence of greater than three, preferably a tetracoordinated phosphorus atom such as a phosphoroselenoate, or an equivalent thereof. Suitable selenizing agents include, for example, potassium selenocyanate (KSeCN), elemental selenium and the like.

Groups $R^6$ and $OR^7$ that can be used in accordance with the present invention can be any suitable group that can protect the trivalent phosphorus attached to either the 2'- or 3'-hydroxy function of the incoming phosphoramidite nucleoside. Examples of phosphorus protecting groups $R^6$ include N,N-dialkylamino groups, such as diisopropylamino, or saturated heterocyclic group having at least one nitrogen atom, optionally with one or more heteroatoms selected from the group consisting of O and S, such as pyrrolidino, piperidino, morpholino, and thiomorpholino; and examples of $OR^7$ include alkoxy groups, such as methoxy, cyanoalkoxy groups, alkenyloxy, trialkylsilylalkoxy, methylsulfonylalkoxy, and arylsulfonylalkoxy, and any combinations thereof. For additional examples of protecting groups, see, for example, U.S. Pat. No. 7,368,550, disclosing protecting groups of the formula:

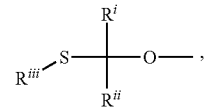

wherein $R^{iii}$ is lower alkyl, modified lower alkyl, or alkyl; $R^i$ and $R^{ii}$ are each independently selected from H, lower alkyl, modified lower alkyl, alkyl, modified alkyl, or aryl.

Figure 10:
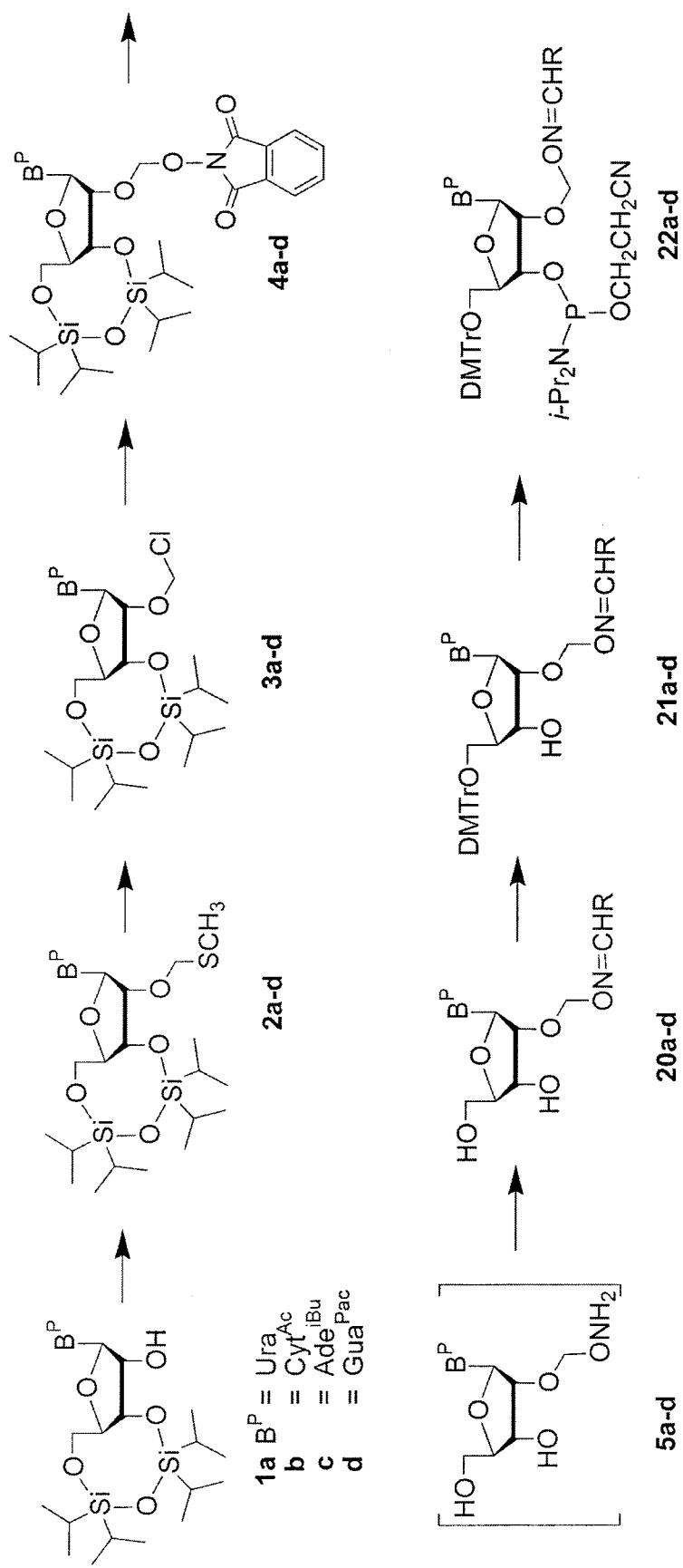
FIG. 10 illustrates some of the reactions steps that can be employed in the preparation of oligonucleotides in accordance with an embodiment of the invention, wherein R=H, —$CH_3$, —$CH_2F$, —$CH_2CN$, —$CH_2OCH_3$, —$CH_2SCH_3$, —$CH_2S(O)CH_3$, —$CH_2SO_2CH_3$, —$CH(CH_3)F$, —$CH(CH_3)CN$, —$CH(CH_3)OCH_3$, —$CH(CH_3)$ $SCH_3$, —$CH(CH_3)S(O)CH_3$, —$CH(CH_3)SO_2CH_3$, —$CY(Z)F$, —$CY(Z)CN$, —$CY(Z)OCH_3$, —$CY(Z)SCH_3$, —$CY(Z)S(O)CH_3$, or —$CY(Z)SO_2CH_3$, where Y is F or $CH_3$ and Z is F or $CH_3$.
Figure 11:
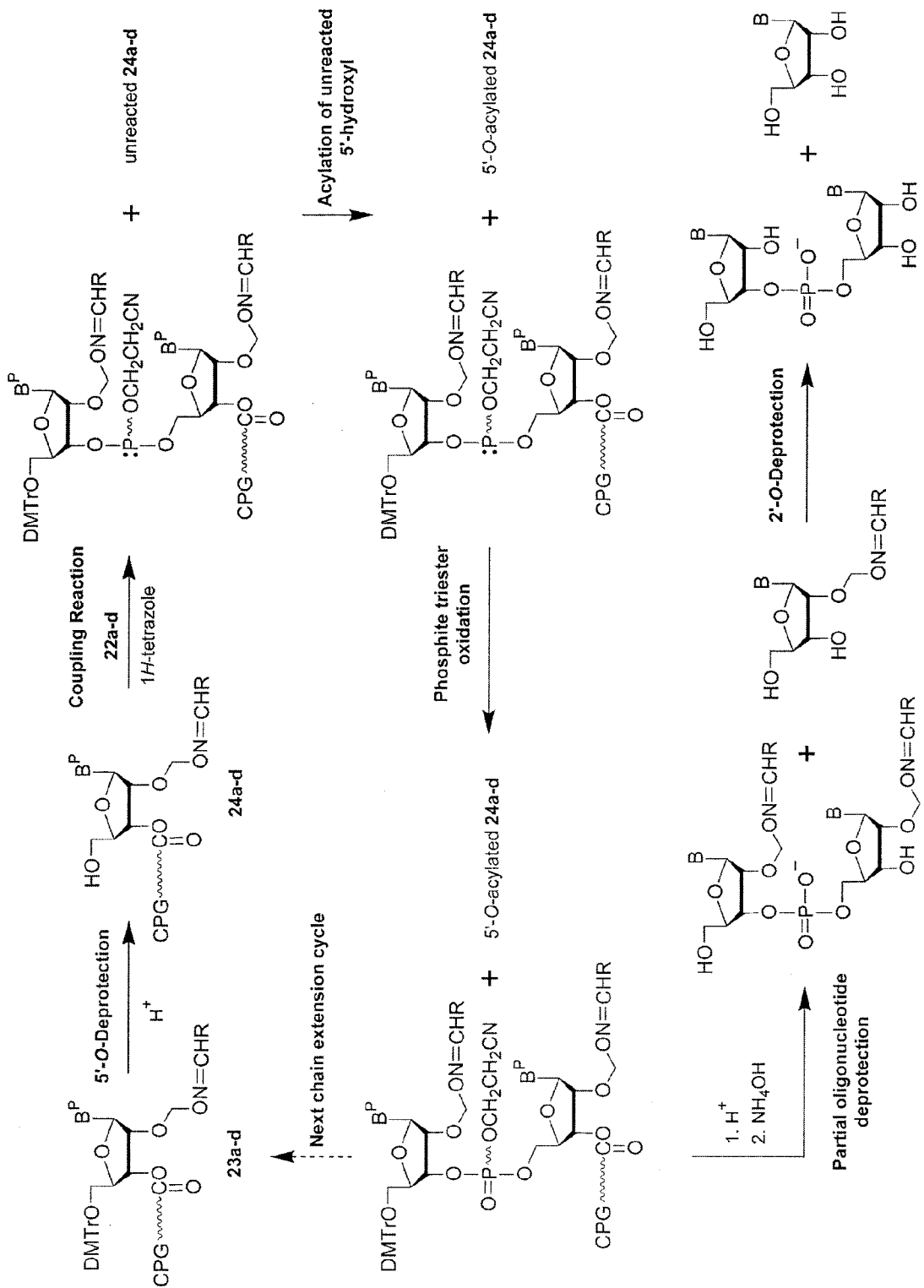
FIG. 11 illustrates further steps that can be employed in the preparation of oligonucleotides in accordance with an embodiment of the invention.

FIG. 10 illustrates some of the reactions steps that can be employed in the preparation of oligonucleotides in accordance with an embodiment of the invention. Compounds, 2a-d, 3a-d, 4a-d, and 5a-d can be prepared as described above from commercial 1a-d. The reaction of 5a with aldehydes in MeOH gave the corresponding 2'-O-methanimine-N-oxymethyl ribonucleoside derivatives 20a (R=H, —CH₃, —CH₂F, —CH₂Cl, —CH₂Br, —CH₂CN, —CH₂OCH₃, —CH₂SCH₃, —CH₂S(O)CH₃, —CH₂SO₂CH₃, —CH(CH₃) F, —CH(CH₃)CN, —CH(CH₃)OCH₃, —CH(CH₃)SCH₃, —CH(CH₃)S(O)CH₃, —CH(CH₃)SO₂CH₃, —C(CH₃)₂Cl, —C(CH$_3$)$_2$Br, —CY(Z)F, —CY(Z)CN, —CY(Z)OCH$_3$, —CY(Z)SCH$_3$, —CY(Z)S(O)CH$_3$, or —CY(Z)SO$_2$CH$_3$, where Y is F or CH$_3$ and Z is F or CH$_3$, in yields of 69% to 82% relative to the molar amounts of 4a used as starting materials. The identities of the ribonucleosides 20a were confirmed by HRMS. Treatment of 20a (R=H, —CH$_3$, —CH$_2$F, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —CH(CH$_3$)OCH$_3$, —CH(CH$_3$)SCH$_3$, —CH(CH$_3$)S(O)CH$_3$, —CH(CH$_3$)SO$_2$CH$_3$, —CY(Z)F, —CY(Z)CN, —CY(Z)OCH$_3$, —CY(Z)SCH$_3$, —CY(Z)S(O)CH$_3$ or —CY(Z)SO$_2$CH$_3$, where Y is F or CH$_3$ and Z is F or CH$_3$) with 4,4'-dimethoxytrityl chloride in anhydrous pyridine afforded 21a (R=H, —CH$_3$, —CH$_2$F, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —CH(CH$_3$)OCH$_3$, —CH(CH$_3$)SCH$_3$, —CH(CH$_3$)S(O)CH$_3$, —CH(CH$_3$)SO$_2$CH$_3$, —CY(Z)F, —CY(Z)CN, —CY(Z)OCH$_3$, —CY(Z)SCH$_3$, —CY(Z)S(O)CH$_3$ or —CY(Z)SO$_2$CH$_3$, where Y is F or CH$_3$ and Z is F or CH$_3$), which were purified by chromatography on silica gel and obtained in yields of 85-95%. The phosphitylation of the ribonucleosides 21a was carried out in anhydrous CH$_2$Cl$_2$ upon addition of Et$_3$N and 2-cyanoethyl N,N-diisopropylchlorophosphoramidite affording the ribonucleoside phosphoramidites 22a (R=H, —CH$_3$, —CH$_2$F, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —CH(CH$_3$)OCH$_3$, —CH(CH$_3$)SCH$_3$, —CH(CH$_3$)S(O)CH$_3$, —CH(CH$_3$)SO$_2$CH$_3$, —CY(Z)F, —CY(Z)CN, —CY(Z)OCH$_3$, —CY(Z)SCH$_3$, —CY(Z)S(O)CH$_3$ or —CY(Z)SO$_2$CH$_3$, where Y is F or CH$_3$ and Z is F or CH$_3$) in yields of 70% to 90% after chromatography on silica gel. FIG. 11 illustrates further steps that can be employed in the preparation of oligonucleotides in accordance with an embodiment of the invention.

Figure 12:
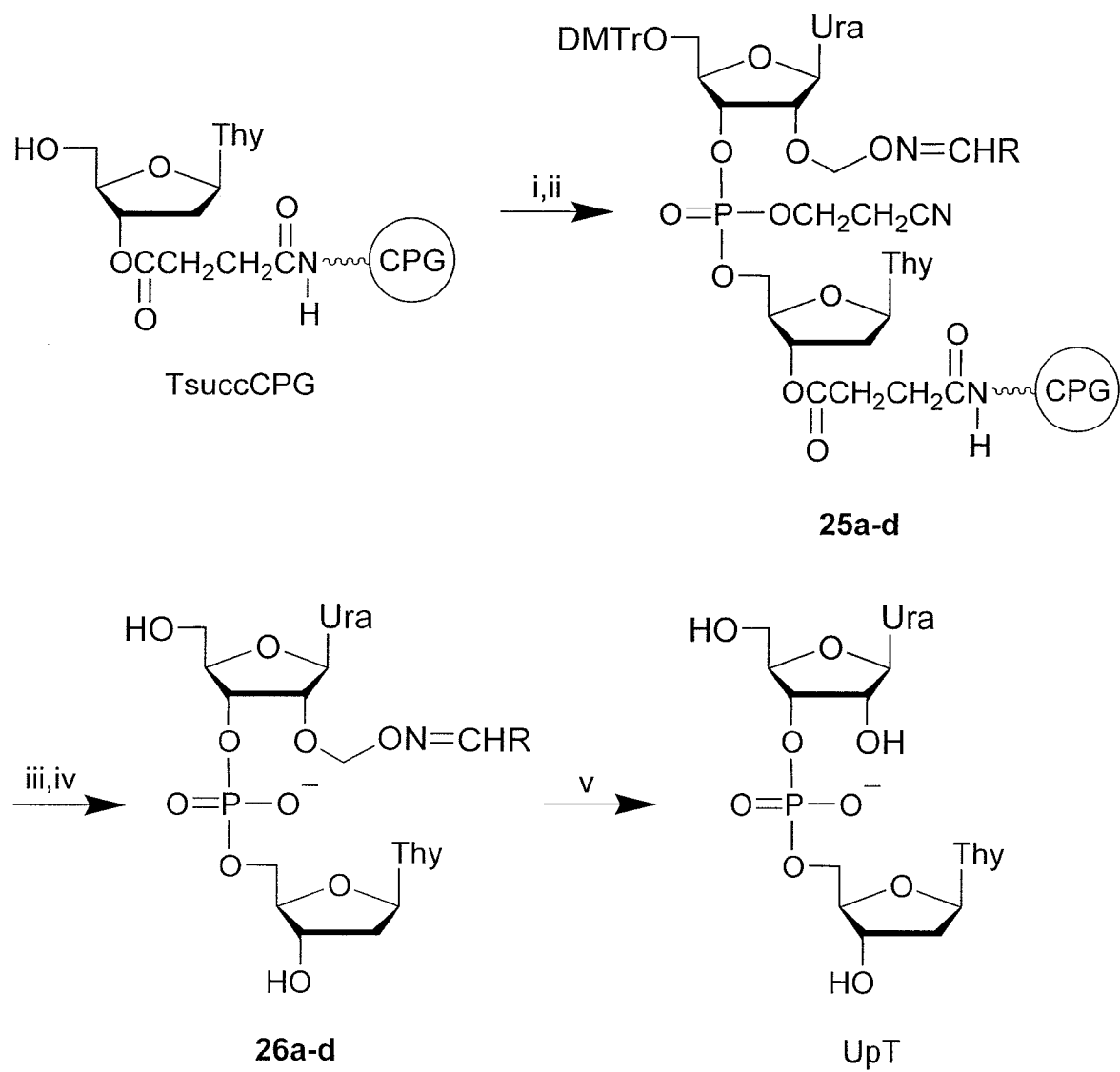
FIG. 12 illustrates a method of solid-phase synthesis of the dinucleoside phosphodiester UpT from the ribonucleoside phosphoramidite 22a (R=H, —$CH_3$, —$CH_2F$, —$CH_2CN$, —$CH_2OCH_3$, —$CH_2SCH_3$, —$CH_2S(O)CH_3$, —$CH_2SO_2CH_3$, —$CH(CH_3)F$, —$CH(CH_3)CN$, —$CH(CH_3)$ $OCH_3$, —$CH(CH_3)$ $SCH_3$, —$CH(CH_3)S(O)CH_3$, —$CH(CH_3)SO_2CH_3$, —$CY(Z)F$, —$CY(Z)CN$, —$CY(Z)OCH_3$, —$CY(Z)SCH_3$, —$CY(Z)S(O)CH_3$, or —$CY(Z)SO_2CH_3$, where Y is F or $CH_3$ and Z is F or $CH_3$). Conditions: (i) 22a, 1H-tetrazole, MeCN, 3 min; (ii) 0.02 M $I_2$ in THF/Pyridine/$H_2O$; (iii) 3% TCA, $CH_2Cl_2$, 3 min; (iv) conc. $NH_3$, 25° C., 30 min; (v) 0.5 M n-$Bu_4NF$, DMSO, 55° C., 1 h; Keys: Ura, uracil-1-yl; Thy, thymin–1-yl; CPG, controlled-pore glass; DMTr, 4,4'-dimethoxytrityl.

FIG. 12 illustrates a method of solid-phase synthesis of the dinucleoside phosphodiester UpT from the ribonucleoside phosphoramidite 22a (R=H, —CH$_3$, —CH$_2$F, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —CH(CH$_3$)OCH$_3$, —CH(CH$_3$)SCH$_3$, —CH(CH$_3$)S(O)CH$_3$, —CH(CH$_3$)SO$_2$CH$_3$, —CY(Z)F, —CY(Z)CN, —CY(Z)OCH$_3$, —CY(Z)SCH$_3$, —CY(Z)S(O)CH$_3$ or —CY(Z)SO$_2$CH$_3$ where Y is F or CH$_3$ and Z is F or CH$_3$). The reaction of each of the ribonucleoside phosphoramidites 22a with thymidine covalently attached to long chain alkylamine controlled-pore glass (LCAA-CPG) through a 3'-O-hemisuccinate linker (TsuccCPG) in the presence of 1H-tetrazole in dry MeCN produced a dinucleoside phosphite triester intermediate, which after treatment with a commercial solution of aqueous iodine provided the dinucleoside phosphate triester 25 (R=H, —CH$_3$, —CH$_2$F, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —CH(CH$_3$)OCH$_3$, —CH(CH$_3$)SCH$_3$, —CH(CH$_3$)S(O)CH$_3$, —CH(CH$_3$)SO$_2$CH$_3$, —CY(Z)F, —CY(Z)CN, —CY(Z)OCH$_3$, —CY(Z)SCH$_3$, —CY(Z)S(O)CH$_3$ or —CY(Z)SO$_2$CH$_3$, where Y is F or CH$_3$ and Z is F or CH$_3$). After complete deblocking of the 5'-hydroxy and phosphate protecting groups, the dinucleoside phosphate diester 26 was released from the solid support under ammonolytic conditions at ambient temperature (~25° C.). Treatment of 26 with 0.5 M tetra-n-butylammonium fluoride in dry DMSO at 25° C. resulted in the complete conversion of 26 to UpT. The ribonucleoside phosphoramidites 22a (R=CH$_2$S(O)CH$_3$) was selected for the solid-phase synthesis of r(Up)$_{20}$dT as an exploratory model for evaluating: (i) phosphoramidite coupling kinetics and coupling efficiencies and; (ii) the fluoride-assisted deblocking kinetics and efficiency of the 2'-hydroxy functions.

In the above embodiments, the group R can include an electron withdrawing group next to Z.

The solid-phase synthesis of the r(Up)$_{20}$dT was carried on a 0.2 μmole scale using 22a as 0.2 M solutions in anhydrous MeCN. 5-Ethylthio-1H-tetrazole was used for activation of 22a in the preparation of r(Up)$_{20}$dT. Under these conditions, the coupling efficiency of 22a averaged 99% over a coupling time of 180 s. The stepwise coupling yields were determined by the standard 4,4'-dimethoxytrityl spectrophotometric assay at 498 nm. After completion of the synthesis the solid-phase-linked 20-mer was treated with coned aqueous NH$_3$ for 30 min at ~25° C. to deblock the 2-cyanoethyl phosphate protecting groups and release the 2'-O-protected r(Up)$_{20}$dT from the solid support. The oligonucleotide was then dissolved in 0.5 M tetra-n-butylammonium fluoride in DMSO; the solution was heated at 55° C. for 48 h. The desalted oligonucleotide r(Up)$_{20}$dT was analyzed by RP-HPLC and characterized by MALDI-TOF mass spectrometry. The RP-HPLC chromatogram of r(Up)$_{20}$dT is shown in FIG. 13 and compared with a RP-HPLC chromatogram of r(Up)$_{20}$dT that was prepared using commercial 2'-O-TBDMS ribonucleoside phosphoramidites under conditions described in the literature (Ogilvie, K. K.; Usman, N.; Nicoghosian, K.; Cedergren, R. *J. Proc. Natl. Acad. Sci. U.S.A.* 1988, 85, 5764-5768).).

The following examples further illustrate the invention but, of course, should not be construed as in any way limiting its scope.

Example 1

This example illustrates a method of preparation of certain intermediates or compounds in accordance with an embodiment of the invention.

Materials and Methods.

Common chemicals and solvents in addition to DMSO, glacial acetic acid, acetic anhydride, potassium carbonate, elemental iodine, sodium bisulfate, pyridine, triethylamine, sulfuryl chloride, N-hydroxyphthalimide, 1,8-diazabicyclo[5.4.0]undec-7-ene (DBU), ammonium fluoride, 1-pyrenecarboxaldehyde, pyrene-1-carbonitrile, 5-cholesten-3-one, D-(+)-biotin 2-nitrophenyl ester, 5-dimethylamino-1-naphthalenesulfonyl chloride (dansyl chloride), 4-(dimethylamino)azobenzene-4'-sulfonyl chloride (dabsyl chloride), aminoacetaldehyde dimethyl acetal, 4-aminobutyraldehyde diethyl acetal, 4-chlorobutyronitrile, and potassium phthalimide were all purchased from commercial sources and used without further purification.

N$^4$-acetyl-5'-O-(1,1,3,3-tetraisopropyldisiloxane-1,3-diyl)cytidine, N$^6$-isobutyryl-5'-O-(1,1,3,3-tetraisopropyldisiloxane-1,3-diyl)adenosine, 5'-O-(1,1,3,3-tetraisopropyldisiloxane-1,3-diyl)uridine, N$^2$-phenoxyacetyl-5'-O-(1,1,3,3-tetraisopropyldisiloxane-1,3-diyl)guanosine, anhydrous solvents (MeCN, CH$_2$Cl$_2$, C$_6$H$_6$, pyridine, THF) and deuterated solvents (C$_6$D$_6$, D$_2$O, DMSO-d$_6$) were obtained from reputable sources and used as received.

Flash chromatography purifications were performed on glass columns (6.0 and 2.5 cm I.D.) packed with silica gel 60 (230-400 mesh), whereas analytical thin-layer chromatography (TLC) analyses were conducted on 2.5 cm×7.5 cm glass plates coated with a 0.25 mm thick layer of silica gel 60 F$_{254}$.

Analytical RP-HPLC analyses were performed using a 5 μm Supelcosil LC-18S column (25 cm×4.6 mm) according to the following conditions: starting from 0.1 M triethylammonium acetate pH 7.0, a linear gradient of 1% MeCN/min is pumped at a flow rate of 1 mL/min for 40 min or, as indicated, starting from 0.1 M triethylammonium acetate pH 7.0, a linear gradient of 1% MeCN/min was pumped at a flow rate of 1 mL/min for 40 min; the gradient was then increased to 6% MeCN/min for 10 min at the same flow rate and kept isocratic for an additional 15 min. In all RP-HPLC chromatograms, peak heights are normalized to the highest peak, which is set to 1 arbitrary unit. 2 M Triethylammonium acetate buffer was purchased from Applied Biosystem and diluted to 0.1 M with HPLC grade water prior to use.

All NMR experiments were performed using a spectrometer at the field of 300.13, 75.47 and 121.5 MHz for one-dimensional $^1$H, $^1$H-decoupled $^{13}$C and $^1$H-decoupled $^{31}$P, respectively. Samples were maintained at a temperature of 298° K. All spectra were recorded in deuterated solvents or as indicated and chemical shifts δ were reported in parts per million (ppm) relative to appropriate internal references.

High resolution mass spectra used to confirm the elemental composition of new compounds were obtained on a Bruker Daltonics ApexQ FT-ICR mass spectrometer equipped with a 12 T magnet. Electrospray ionization in positive ion mode was used to generate [M+H]$^+$ and [M+Na]$^+$ ions out of test samples (0.01 mg dissolved in 1 mL of 10 mM ammonium acetate in MeCN:H$_2$O (1:1 v/v)). Spectra were externally calibrated using 0.5 mg/mL solution of CsI in water, which yielded a series of peaks in the mass range used for analysis (200-2000 m/z).

3',5'-O-(1,1,3,3-Tetraisopropyldisiloxane-1,3-diyl)-2'-O-(methylthiomethyl)uridine (2a)

The preparation of 2a was performed with minor modifications of a published procedure (Cieślak, J., et al., *J. Org. Chem.* 2008, 73, 2774-2783). To a solution of commercial 5'-O-(1,1,3,3-tetraisopropyldisiloxane-1,3-diyl)uridine (1a, 7.3 g, 15 mmol) in DMSO (15 mL) was added glacial AcOH (23 mL) and Ac$_2$O (15 mL). The solution was stirred at 50±2° C. until completion of the reaction (~16 h), which was monitored by TLC (CHCl$_3$/MeOH 95:5 v/v). The solution was transferred to a 2 L Erlenmeyer flask to which was added, under vigorous stirring, a solution of K$_2$CO$_3$ (31 g) in water (200 mL). The precipitated material was isolated either by filtration or decantation and was redissolved in a minimum volume of THF (15-20 mL). The resulting solution was then poured into water (250 mL) to give the crude product as a gummy material. Most of the water was decanted; the crude product was carefully dried by consecutive co-evaporation with pyridine (30 mL), toluene (3×30 mL) and dichloromethane (30 mL). The crude ribonucleoside 2a was purified by chromatography on silica gel (~150 g in a 6.5 cm [I.D.] glass column) using a gradient of MeOH (0→3%) in CH$_2$Cl$_2$ as the eluent. Fractions containing pure 2a (TLC) were collected, evaporated to a foam under low pressure, and dissolved in dry C$_6$H$_6$ (~20 mL); the solution was frozen and then lyophilized under high vacuum affording a white powder (7 g, 12.8 mmol, 85%). Characterization data obtained from $^1$H and $^{13}$C NMR analysis of 2a are in agreement with those reported by Semenyuk et al., *J. Am. Chem. Soc.* 2006, 128, 12356-12357.

3',5'-O-(1,1,3,3-Tetraisopropyldisiloxane-1,3-diyl)-2'-O-(phthalimidooxymethyl)uridine (4a)

To a solution of thoroughly dried 2a (1.1 g, 2.0 mmol) in anhydrous dichloromethane (20 mL) was added neat sulfuryl chloride (2.20 mmol, 176 µL); the solution was stirred at ~25° C. for 2 h and was then concentrated under reduced pressure to give the 2'-O-chloromethyluridine derivative 3a as an amorphous solid. N-Hydroxyphthalimide (1.3 g, 8.0 mmol) was placed into a separate reaction vessel to which was added anhydrous CH$_2$Cl$_2$ (10 mL) and DBU (1.04 mL, 7.00 mmol). After 10 min, the red solution was added to unpurified 3a; the reaction mixture was kept stirring at ~25° C. for 24 h to which was then added CH$_2$Cl$_2$ (80 mL). The solution was vigorously mixed with aqueous 1 M acetic acid (20 mL); the aqueous layer was discarded and the organic phase was washed twice with a saturated aqueous solution of NaHCO$_3$ (20 mL). The organic layer was collected, dried over anhydrous Na$_2$SO$_4$, filtered, and evaporated to a foamy solid under reduced pressure. The crude product 4a was purified by chromatography on silica gel (~35 g in a 2.5-cm [I.D.] glass column) using a gradient of MeOH (0→3%) in CH$_2$Cl$_2$ as the eluent. Fractions containing 4a were collected and evaporated under vacuum to give a solid (1.24 mg, 1.88 mmol) in a yield of 94% based on the molar amount of starting material (2a) that was used $^1$H NMR (300 MHz, DMSO-d$_6$): δ 11.41 (d, J=2.2 Hz, 1H), 7.88-7.80 (m, 4H), 7.65 (d, J=8.2 Hz, 1H), 5.62 (dd, J=8.2, 2.2 Hz, 1H), 5.39 (d, J=7.2 Hz, 1H), 5.34 (d, J=7.2 Hz, 1H), 4.87 (d, J=5.2 Hz, 1H), 4.63 (dd, J=5.2, 5.2 Hz, 1H), 4.03 (dd, J=13.0, 3.0 Hz, 1H), 3.90 (dd, J=13.0, 3.0 Hz, 1H), 3.79 (dt, J=9.0, 3.0 Hz, 1H), 1.07-0.95 (m, 28H). $^{13}$C NMR (75 MHz, DMSO-d$_6$): δ 163.2, 163.0, 150.0, 142.6, 134.8, 128.4, 123.3, 101.3, 98.0, 90.6, 80.2, 77.9, 69.8, 60.2, 17.2, 17.1, 17.0, 16.81, 16.77, 16.7, 12.5, 12.3, 12.1, 12.0. +ESI-HRMS: Calcd for C$_{30}$H$_{43}$N$_3$O$_{10}$Si$_2$ [M+H]$^+$ 662.2560. found 662.2560.

2'-O-(Aminooxymethyl)uridine (5a)

Purified 4a (330 mg, 500 µmmol) was dissolved in methanol (3 mL), and ammonium fluoride (185 mg, 5.00 µmol) was added. The heterogeneous reaction mixture was stirred at ~25° C. until complete desilylation and removal of the phthalimido group was obtained (~16 h) as indicated by TLC (CHCl$_3$/MeOH 9:1 v/v). The reaction product was purified by silica gel chromatography using a gradient of MeOH (0→12%) in CH$_2$Cl$_2$ as the eluent. Fractions containing the product were collected, evaporated to dryness to provide 5a. $^1$H NMR (300 MHz, DMSO-d$_6$): δ 11.4 (bs, 1H), 7.93 (d, J=8.1 Hz, 1H), 6.21 (bs, 2H), 5.87 (d, J=4.4 Hz, 1H), 5.64 (d, J=8.1 Hz, 1H), 5.17 (t, J=4.9 Hz, 1H), 4.74 (s, 2H), 4.11 (m, 2H), 3.88 (m, 1H), 3.65 (ddd, J=12.0, 5.0, 3.1 Hz, 1H), 3.56 (ddd, J=12.0, 5.0, 3.1 Hz, 1H), 3.16 (d, J=5.0 Hz). $^{13}$C NMR (75 MHz, DMSO-d$_6$): δ 163.1, 150.7, 140.4, 101.8, 98.0, 86.7, 84.9, 79.1, 69.0, 60.4. +ESI-HRMS: Calcd for C$_{10}$H$_{15}$N$_3$O$_7$ [M+H]$^+$ 290.0983. found 290.0986.

2'-O-(Pyren-1-ylmethanimine-N-oxymethyl)uridine (6a)

2'-O-(Aminooxymethyl)uridine (5a) was prepared from 4a at the scale and under conditions identical to those described above. After complete NH$_4$F-mediated desilylation and removal of the phthalimido group in MeOH, 1-pyrenecarboxaldehyde (2.00 mmol, 460 mg) was added to the reaction mixture, which was then heated at 55±2° C. in a 4-mL screw-capped vial until completion of the oximation reaction (1 h) as indicated by TLC (CHCl$_3$/MeOH 9:1 v/v). The reaction mixture was transferred to a 20-mL screw-cap glass vial to which was added CH$_2$Cl$_2$ (7 mL) and a saturated aqueous solution of NaHCO$_3$ (2 mL); after vigorous shaking the organic phase was collected and evaporated to dryness under vacuum. The pyrenylated ribonucleoside 6a was purified by chromatography on silica gel employing a gradient of MeOH (0→8%) in CH$_2$Cl$_2$ as the eluent. Fractions containing the pure product were collected, evaporated to dryness under reduced pressure affording 6a as a yellowish powder (206 mg, 410 µmol) in a yield of 82% based on the molar amount of starting material (4a) that was used. +ESI-HRMS: Calcd for C$_{27}$H$_{23}$N$_3$O$_7$ [M+H]$^+$ 502.1609. found 502.1609.

N$^4$-Acetyl-3',5'-O-(1,1,3,3-tetraisopropyldisiloxane-1,3-diyl)-2'-O-(methylthiomethyl)cytidine (2b)

The preparation of 2b was performed with minor modifications of a published procedure. Cieślak, J. et al. supra. To a solution of commercial N$^4$-acetyl-5'-O-(1,1,3,3-tetraisopropyldisiloxane-1,3-diyl)cytidine (1b, 7.9 g, 15 mmol) in DMSO (15 mL) was added glacial AcOH (15 mL) and Ac$_2$O (10 mL). The solution was stirred at 50±2° C. until completion of the reaction (~16 h), which was monitored by TLC (CHCl$_3$/MeOH 95:5 v/v). The solution was transferred to a 2 L Erlenmeyer flask to which was added, under vigorous stirring, a solution of K$_2$CO$_3$ (31.2 g) in water (240 mL). The precipitated material was worked-up, purified and processed under conditions identical to those employed in the preparation, purification and processing of 2a. The ribonucleoside 2b was isolated as a white solid (8.30 g, 14.1 mmol) in a yield of 94%. $^1$H NMR (300 MHz, DMSO-d$_6$): δ 11.08 (s, 1H), 8.19 (d, J=7.5 Hz, 1H), 7.35 (d, J=7.5 Hz, 1H), 5.77 (s, 1H), 5.14 (d, J=11.2 Hz, 1H), 5.04 (d, J=11.2 Hz, 1H), 4.44 (d, J=4.4 Hz, 1H), 4.22 (m, 3H), 3.93 (dd, J=13.6, 1.9 Hz, 1H), 2.16 (s, 3H), 2.14 (s, 3H), 1.08-0.95 (m, 28H). $^{13}$C NMR (75 MHz, DMSO-d$_6$): δ 170.9, 162.6, 154.1, 143.1, 95.0, 88.9, 81.3, 77.0, 73.0, 67.0, 59.2, 24.2, 17.1, 17.0, 16.9, 16.9, 16.8, 16.7, 16.5, 12.6, 12.4, 12.3, 12.2, 11.8. +ESI-HRMS: Calcd for C$_{25}$H$_{45}$N$_3$O$_7$SSi$_2$ [M+H]$^+$ 580.2590. found 580.2597.

N$^4$-Acetyl-3',5'-O-(1,1,3,3-tetraisopropyldisiloxane-1,3-diyl)-2'-O-(phthalimidooxymethyl)cytidine (4b)

The preparation and purification of 4b were performed at a scale and under conditions identical to those described above for the preparation and purification of 4a. The ribonucleoside 4b was obtained as a solid (1.04 g, 1.48 mmol) in a yield of 74% based on the amount of starting material (2b) that was used. $^1$H NMR (300 MHz, DMSO-d$_6$): δ 10.98 (s, 1H), 8.10 (d, J=7.5 Hz, 1H), 7.87-7.80 (m, 4H), 7.22 (d, J=7.5 Hz, 1H), 5.76 (s, 1H), 5.52 (d, J=7.0 Hz, 1H), 5.45 (d, J=7.0 Hz, 1H), 4.70 (d, J=4.8 Hz, 1H), 4.41 (dd, J=4.8, 4.8 Hz, 1H), 4.15 (dd, J=12.9, 1.2 Hz, 1H), 4.00-3.88 (m, 2H), 2.10 (s, 3H), 1.04-0.89 (m, 28H). $^{13}$C NMR (75 MHz, DMSO-d$_6$): δ 171.0, 162.9, 162.7, 154.0, 145.2, 134.7, 134.2, 128.5, 123.2, 122.9, 98.1, 95.0, 90.1, 80.8, 79.3, 68.3, 59.7, 24.3, 17.2, 17.12, 17.09, 17.0, 16.8, 16.7, 16.6, 12.5, 12.3, 12.2, 11.9. +ESI-HRMS: Calcd for C$_{32}$H$_{46}$N$_4$O$_{10}$Si$_2$ [M+☐☐☐H]$^+$ 703.2825. found 703.2825.

2'-O-(Aminooxymethyl)cytidine (5b)

Silica gel-purified 4b (351 mg, 500 µmol) was dissolved in methanol (3 mL), and ammonium fluoride (185 mg, 5.00 mmol) was added. The heterogeneous reaction mixture was stirred at ~25° C. until complete desilylation and removal of phthalimido group was obtained (~16 h) as indicated by TLC (CHCl$_3$/MeOH 9:1 v/v). A stream of air was used to remove MeOH from the reaction mixture and was followed by the addition of commercial concentrated (28%) aqueous NH$_3$ (3 mL); the resulting solution was kept at 55° C. for 1 h in a tightly closed 4-mL screw cap glass vial. Excess ammonia was removed under a stream of air; the material left was purified by silica gel chromatography using a gradient of MeOH (0→25%) in CH$_2$Cl$_2$ as the eluent. Fractions containing the product were collected, evaporated to dryness under low pressure to give 5b. $^1$H NMR (300 MHz, DMSO-d$_6$): δ 7.92 (d, J=7.4 Hz, 1H), 7.26 (m, 2H), 5.83 (d, J=3.2 Hz, 1H), 5.74 (d, J=7.4 Hz, 1H), 5.15 (br s, 1H), 4.77 (q, J=7.2 Hz, 2H), 4.04 (m, 2H), 3.84 (m, 2H), 3.70 (dd, J=12.2, 2.2 Hz, 1H), 3.70 (dd, J=12.2, 2.7 Hz, 1H). $^{13}$C NMR (75 MHz, DMSO-d$_6$): δ 165.6, 155.3, 140.9, 97.7, 94.0, 88.2, 83.9, 79.3, 68.3, 59.9. +ESI-HRMS: Calcd for C$_{10}$H$_{16}$N$_4$O$_6$ [M☐☐☐+H]$^{+☐}$ 289.1143. found 289.1145.

2'-O-(Pyren–1-ylmethanimine-N-oxymethyl)cytidine (6b)

2'-O-(Aminooxymethyl)cytidine (5b) was prepared from 4b at a scale and under conditions identical to those described above. After removal of excess ammonia, the material left was suspended in MeOH (3 mL) and 1-pyrenecarboxaldehyde (460 mg, 2.00 mmol) was added to the suspension in a 4-mL screw-capped glass vial. The reaction mixture was heated at ~55° C. until completion of the oximation reaction (1 h), transferred to a 20-mL screw-cap glass vial and diluted by adding CH$_2$Cl$_2$ (7 mL) and a saturated aqueous solution of NaHCO$_3$ (2 mL). After vigorous shaking, the organic phase was collected and evaporated to dryness under low pressure. The pyrenylated ribonucleoside 6b was purified by chromatography on silica gel employing a gradient of MeOH (0→8%) in CH$_2$Cl$_2$ as the eluent. Fractions containing the pure product were collected, evaporated to dryness under reduced pressure affording 6b as a yellow powder (188 mg, 375 µmol) in a yield of 75% based on the molar amount of starting material (4b) that was used+ESI-HRMS: Calcd for C$_{27}$H$_{24}$N$_4$O$_6$ [M+H]$^+$ 501.1769. found 501.1769.

N$^6$-Isobutyryl-3',5'-O-(1,1,3,3-tetraisopropyldisiloxane-1,3-diyl)-2'-O-(methylthiomethyl) adenosine (2c)

The preparation of 2c was performed with minor modifications of a published procedure. Cieślak, J., et al. supra. To a solution of commercial N$^6$-isobutyryl-5'-O-(1,1,3,3-tetraisopropyldisiloxane-1,3-diyl)adenosine (1c, 8.7 g, 15 mmol,) in DMSO (23 mL) was added glacial AcOH (23 mL) and Ac$_2$O (15 mL). The solution was stirred at 50±2° C. until completion of the reaction (~16 h), which was monitored by TLC (CHCl$_3$/MeOH 95:5 v/v). The solution was transferred to a 2 L Erlenmeyer flask to which was added, under vigorous stirring, a solution of K$_2$CO$_3$ (46.2 g) in water (231 mL). The precipitated material was worked-up and purified under conditions identical to those employed in the preparation, purification and processing of 2a. The ribonucleoside 2c was isolated as a white solid (8.5 g, 13.3 mmol) in a yield of 89%. $^1$H NMR (300 MHz, DMSO-d$_6$): δ 10.69 (s, 1H), 8.56 (s, 1H), 8.49 (s, 1H), 6.11 (d, J=1 Hz, 1H), 5.00 (dd, J=5.3, 5.2 Hz, 1H), 4.97 (d, J=11.4 Hz, 1H), 4.91 (d, J=11.4 Hz, 1H), 4.89 (d, J=4.8 Hz, 1H), 4.08 (dd, J=12.9, 2.5 Hz, 1H), 4.02 (dt, J=9.0, 2.5, Hz, 1H), 3.93 (dd, J=12.9, 2.3 Hz, 1H), 2.96 (sept, J=6.7 Hz, 1H), 2.08 (s, 3H), 1.12 (d, J=6.7 Hz, 6H), 1.09-0.97 (m, 28H). $^{13}$C NMR (75 MHz, DMSO-d$_6$): δ 175.2, 151.4, 150.8, 149.9, 142.6, 124.1, 87.6, 80.8, 76.7, 73.7, 69.3, 59.9, 34.2, 19.1, 17.2, 17.1, 17.0, 16.9, 16.8, 16.7, 12.7, 12.6, 12.3, 12.1, 11.9. +ESI-HRMS: Calcd for C$_{28}$H$_{49}$N$_5$O$_6$SSi$_2$ [M+H]$^+$ 640.3015. found 640.3016.

N$^6$-Isobutyryl-3',5'-O-(1,1,3,3-tetraisopropyldisiloxane-1,3-diyl)-2'-O-(phthalimidooxymethyl) adenosine (4c)

The preparation and purification of 4c were performed at a scale and under conditions identical to those described above for the preparation and purification of 4a. The ribonucleoside 4c was obtained as a solid (1.24 g, 1.64 mmol) in a yield of 82% based on the molar amount of the starting material (2c) that was used. $^1$H NMR (300 MHz, DMSO-d$_6$): δ 10.72 (s, 1H), 8.59 (s, 1H), 8.45 (s, 1H), 7.84-7.74 (m, 4H), 6.06 (d, J=1.1 Hz, 1H), 5.45 (d, J=7.5 Hz, 1H), 5.37-5.30 (m, 3H), 4.04-3.89 (m, 3H), 2.97 (sept, J=6.8 Hz, 1H), 1.15 (d, J=6.8 Hz, 3H), 1.14 (d, J=6.8 Hz, 3H), 1.04-0.96 (m, 28H). $^{13}$C NMR (75 MHz, DMSO-d$_6$): δ 175.2, 163.0, 151.2, 150.9, 149.9, 144.3, 134.8, 134.2, 128.3, 124.3, 123.2, 122.9, 98.4, 87.7, 80.2, 77.8, 70.3, 59.9, 34.3, 19.2, 19.1, 17.1, 17.0, 16.9, 16.8, 16.7, 12.6, 12.3, 12.1. +ESI-HRMS: Calcd for C$_{35}$H$_{50}$N$_6$O$_9$Si$_2$ [M+H]$^+$ 755.3251. found 755.3250.

2'-O-(Aminooxymethyl)adenosine (5c)

The preparation of 5c from 4c was performed at a scale and under conditions identical to those used for the preparation of 5b. After removal of excess ammonia under a stream of air, 2'-O-(aminooxymethyl)adenosine was purified by silica gel chromatography employing a gradient of MeOH (0→10%) in $CH_2Cl_2$ as the eluent. Fractions containing the product were collected and evaporated to dryness under low pressure affording 5c. $^1$H NMR (300 MHz, DMSO-$d_6$): δ 8.38 (s, 1H), 8.13 (s, 1H), 7.37 (bs, 2H), 6.21 (bs, 2H), 6.06 (d, J=6.0 Hz, 1H), 5.43 (m, 2H), 4.68 (q, J=7.3 Hz, 2H), 4.67 (m, 1H), 4.33 (br s, 1H), 3.99 (q, J=3.4 Hz, 1H), 3.68 (m, 1H), 3.57 (m, 1H). $^{13}$C NMR (75 MHz, DMSO-$d_6$): δ 156.1, 152.4, 148.9, 139.7, 119.2, 98.2, 86.3, 86.1, 79.3, 69.8, 61.4. +ESI-HRMS: Calcd for $C_{11}H_{16}N_6O_5$ [M+H]$^+$ 313.1255. found 313.1256.

2'O-(Pyren–1-ylmethanimine-N-oxymethyl)adenosine (6c)

The preparation of 5c from 4c was performed at a scale and under conditions identical to those described above. After removal of excess ammonia, the material left was reacted with 1-pyrenecarboxaldehyde at a scale and under condition identical to those employed for the preparation of 6b. The pyrenylated ribonucleoside 6c was purified by silica gel chromatography under conditions identical to those described for the purification of 6b and was obtained in a yield of 77% (200 mg, 385 μmol) based on the molar amount of starting material (4c) that was used. +ESI-HRMS: Calcd for $C_{28}H_{24}N_6O_5$ [M+H]$^+$ 525.1881. found 525.1882.

N$^2$-Phenoxyacetyl-3',5'-O-(1,1,3,3-tetraisopropyldisiloxane-1,3-diyl)-2'-O-(methylthiomethyl) guanosine (2d)

The preparation of 2d was performed with minor modifications of a published procedure. Cieślak, J., et al. supra. To a solution of commercial N$^2$-phenoxyacetyl-5'-O-(1,1,3,3-tetraisopropyldisiloxane-1,3-diyl)guanosine (1d, 9.9 g, 15 mmol) in DMSO (22.5 mL) was added glacial AcOH (22.5 mL) and $Ac_2O$ (15.0 mL). The solution was stirred at 50±2° C. until completion of the reaction (~16 h), which was monitored by TLC ($CHCl_3$/MeOH 95:5 v/v). The solution was transferred to a 2 L Erlenmeyer flask to which was added, under vigorous stirring, a solution of $K_2CO_3$ (51.0 g) in water (270 mL). The precipitated material was worked-up and purified under conditions identical to those employed in the preparation, purification and processing of 2a. The ribonucleoside 2d was isolated as a white solid (9.3 g, 13 mmol) in a yield of 87%. $^1$HNMR (300 MHz, DMSO-$d_6$): δ 11.84 (bs, 1H), 11.83 (bs, 1H), 8.05 (s, 1H), 7.32 (d, J=7.6 Hz, 1H), 7.30 (d, J=8.4 Hz, 1H), 6.98 (m, 3H), 5.91 (d, J=1.1 Hz, 1H), 4.95 (s, 2H), 4.84 (s, 2H), 4.52 (m, 2H), 4.16 (dd, J=12.9, 2.5 Hz, 1H), 4.06 (dt, J=8.2, 2.5 Hz, 1H), 3.95 (dd, J=12.9, 2.5 Hz, 1H), 2.08 (s, 3H), 1.06-0.95 (m, 28H). $^{13}$C NMR (75 MHz, DMSO-$d_6$): δ 170.7, 157.5, 154.8, 147.6, 147.3, 136.1, 129.4, 121.3, 120.5, 114.5, 86.5, 81.3, 77.8, 73.8, 68.8, 66.2, 60.0, 17.2, 17.16, 17.13, 17.1, 17.05, 17.03, 16.8, 16.74, 16.70, 12.8, 12.7, 12.6, 12.3, 12.2, 11.9. +ESI-HRMS: Calcd for $C_{32}H_{49}N_5O_8SSi_2$ [M+H]$^+$ 720.2913. found 720.2918.

N$^2$-Phenoxyacetyl-3',5'-O-(1,1,3,3-tetraisopropyldisiloxane-1,3-diyl)-2'-O-(phthalimidooxymethyl) guanosine (4d)

The preparation and purification of 4d were performed at a scale and under conditions identical to those described above for the preparation and purification of 4a. The ribonucleoside 4d was obtained as a solid (1.10 g, 1.32 mmol) in a yield of 66% based on the molar amount of starting material (2d) that was used. $^1$HNMR (300 MHz, DMSO-$d_6$): δ 11.81 (br s, 1H), 11.55 (br s, 1H), 8.15 (s, 1H), 7.85-7.70 (m, 4H), 7.34-7.28 (m, 3H), 6.99-6.94 (m, 3H), 5.94 (d, J=1.3 Hz, 1H), 5.48 (d, J=7.0 Hz, 1H), 5.39 (d, J=7.0 Hz, 1H), 5.48 (dd, J=5.2, 1.2 Hz, 1H), 4.75 (m, 2H), 4.64 (m, 1H), 4.07-3.89 (m, 3H), 1.07-0.95 (m, 28H). $^{13}$C NMR (75 MHz, DMSO-$d_6$): δ 170.5, 162.9, 157.5, 154.9, 148.1, 147.2, 137.2, 134.8, 129.5, 128.3, 123.2, 121.3, 114.5, 98.4, 86.0, 80.7, 78.6, 70.2, 66.2, 60.1, 17.2, 17.1, 16.9, 16.8, 12.8, 12.6, 12.3, 12.05, 12.02. +ESI-HRMS: Calcd for $C_{39}H_{50}N_6O_{11}Si_2$ [M+H]$^+$ 835.3149. found 835.3148.

2'-O-(Aminooxymethyl)guanosine (5d)

The preparation of 5d from 4d was performed under conditions identical to those used for the preparation of 5b. After removal of excess ammonia under a stream of air, 2'-O-(aminooxymethyl)guanosine was purified by silica gel chromatography using a gradient of MeOH (0→25%) in $CH_2Cl_2$ as the eluent. Fractions containing the product were collected, evaporated to dryness under reduced pressure providing 5d. $^1$H NMR (300 MHz, DMSO-$d_6$): δ 10.77 (br s, 1H), 7.96 (s, 1H), 6.59 (bs, 2H), 5.85 (d, J=6.0 Hz, 1H), 5.12 (t, J=5.2 Hz, 1H), 4.72 (m, 2H), 4.46 (dd, J=6.0, 5.7 Hz, 1H), 4.26 (dd, J=4.8, 4.8 Hz, 1H), 3.91 (q, J=3.8 Hz, 1H), 3.61 (dt, J=11.8, 4.4 Hz, 1H), 3.52 (dt, J=11.8, 4.4 Hz, 1H). $^{13}$C NMR (75 MHz, DMSO-$d_6$): δ 156.6, 153.8, 151.1, 135.3, 116.5, 98.0, 85.6, 84.8, 79.6, 69.6, 61.1. +ESI-HRMS: Calcd for $C_{11}H_{16}N_6O_6$ [M+H]$^+$ 329.1204. found 329.1211.

2'-O-(Pyren–1-ylmethanimine-N-oxymethyl)guanosine (6d)

The preparation of 5d from 4d was performed at a scale and under conditions identical to those used described above. After removal of excess ammonia, the material left was reacted with 1-pyrenecarboxaldehyde at a scale and under condition identical to those employed for the preparation of 6b. The pyrenylated ribonucleoside 6d was purified by silica gel chromatography under conditions identical to those described for the purification of 6b and was obtained in a yield of 69% (187 mg, 345 μmol) based on the molar amount of starting material (4d) that was used. +ESI-HRMS: Calcd for $C_{28}H_{24}N_6O_6$ [M+H]$^+$ 541.1830. found 541.1829.

2'-O-(5-Cholesten-3-imine-N-oxymethyl)uridine (8)

2'-O-(Aminooxymethyl)uridine (5a) was prepared as described above from silica gel-purified 4a (132 mg, 200 μmol). After complete $NH_4F$-mediated desilylation and removal of the phthalimido group, 5-cholesten-3-one (7, 154 mg, 4.00 μmol) was added to the reaction mixture, which was then heated at 55±2° C. in a 4-mL screw-capped vial until completion of the oximation reaction (1 h) as indicated by TLC ($CHCl_3$/MeOH 9:1 v/v). The reaction mixture was transferred to a 20-mL screw-cap glass vial to which was added $CH_2Cl_2$ (7 mL) and a saturated aqueous solution of $NaHCO_3$ (2 mL); after vigorous mixing the organic phase was collected and evaporated to dryness under vacuum. The product was purified by chromatography on silica gel using a gradient of MeOH (0→4%) in $CH_2Cl_2$ as the eluent. Fractions containing the pure product were collected, evaporated to dryness under reduced pressure giving 8 as a white powder (90 mg, 0.14 mmol) in a yield of 69% based on the molar amount of starting material (4a) that was used. +ESI-HRMS: Calcd for $C_{37}H_{57}N_3O_7$ [M+H]$^+$ 656.4269. found 656.4269.

N-(2,2-Dimethoxyethyl)biotinamide (9)

To a suspension of D-(+)-biotin 2-nitrophenyl ester (365 mg, 1.00 mmol) in MeCN (20 mL) was added aminoacetaldehyde dimethyl acetal (130 μL, 1.20 mmol) and $Et_3N$ (170 μL, 1.20 mmol). The suspension was gently heated until a solution was obtained; the solution was then stirred for 16 h at ~25° C. The reaction mixture was evaporated to dryness under reduced pressure and the material left was purified by silica gel chromatography using a gradient of MeOH (0→10%) in $CH_2Cl_2$ as the eluent. Fractions containing the product were collected and evaporated to dryness under low pressure affording 9 (300 mg, 910 µmol) as a solid in a yield of 91%. $^1$H NMR (300 MHz, DMSO-$d_6$): δ 7.87 (t, J=5.8 Hz, 1H), 6.43 (s, 1H), 6.37 (s, 1H), 4.32 (t, J=5.5 Hz, 1H), 4.28 (d, J=5.5 Hz, 1H), 4.12 (ddd, J=7.6, 4.4, 1.8 Hz, 1H), 3.25 (s, 6H), 3.13 (t, J=5.7 Hz, 2H), 2.82 (dd, J=12.3, 12.3 Hz, 1H), 2.56 (d, J=12.3 Hz, 1H), 2.07 (t, J=7.4 Hz, 2H), 1.66-1.22 (m, 7H). $^{13}$C NMR (75 MHz, DMSO-$d_6$): δ 172.2, 162.6, 102.0, 61.0, 59.1, 55.4, 53.1, 40.2, 39.8, 34.9, 28.1, 28.0, 25.2. +ESI-HRMS: Calcd for $C_{14}H_{25}N_3O_4S$ $[M+H]^+$ 332.1639. found 332.1641.

N-(2-Oxoethyl)biotinamide

N-(2,2-Dimethoxyethyl)biotinamide (9, 280 mg, 850 µmol) was dissolved in MeOH (2 mL) and conc. HCl (0.5 mL) was added to the solution, which was allowed to stir for 1 h at 25° C. The reaction mixture was evaporated to dryness under reduced pressure to yield the aldehyde, the total amount of which was used without further purification in the preparation of 10.

The biotinylated uridine conjugate 10

2'-O-(Aminooxymethyl)uridine (5a) was prepared from silica gel-purified 4a at a scale and under conditions identical to those described for the preparation of 8. After complete $NH_4F$-mediated desilylation and removal of the phthalimido group, a solution of all the N-(2-oxoethyl)biotinamide produced above in MeOH (2 mL) was added to the reaction mixture, which was heated at 55±2° C. in a 4-mL screw-capped vial until completion of the oximation reaction (1 h) as indicated by TLC ($CHCl_3$/MeOH 9:1 v/v). The reaction mixture was then worked-up and processed exactly as described in the preparation of 8. The product was purified by chromatography on silica gel employing a gradient of MeOH (0→20%) in $CH_2Cl_2$ as the eluent. Fractions containing the pure product were collected, evaporated to dryness under reduced pressure providing 10 as a white powder (74 mg, 0.13 mmol) in a yield of 66% based on the molar amount of starting material (4a) that was employed. +ESI-HRMS: Calcd for $C_{22}H_{32}N_6O_9S$ $[M+H]^+$ 557.2024. found 557.2024.

N-(2,2-Dimethoxyethyl)-5-(dimethylamino)naphthalene-1-sulfonamide (11)

To a solution of dansyl chloride (270 mg, 1.00 mmol) in $CH_2Cl_2$ (10 mL) was added aminoacetaldehyde dimethyl acetal (130 µL, 1.2 mmol) and $Et_3N$ (170 µL, 1.2 mmol); the solution was allowed to stir for 1 h at 25° C. The reaction mixture was then evaporated to dryness under reduced pressure and the material left was purified by silica gel chromatography using a gradient of MeOH (0→1%) in $CH_2Cl_2$ as the eluent. Fractions containing the product were collected and evaporated to dryness under low pressure affording 11 (318 mg, 940 µmol) as a solid in a yield of 94%. $^1$H NMR (300 MHz, DMSO-$d_6$): δ 8.45 (dt, J=8.5, 1.1 Hz, 1H), 8.29 (dt, J=8.8, 0.9 Hz, 1H), 8.16 (t, J=5.5 Hz, 1H), 8.10 (dd, J=7.3, 1.1 Hz, 1H), 7.61 (t, J=8.5 Hz, 1H), 7.58 (t, J=8.5 Hz, 1H), 7.25 (dd, J=7.6, 0.7 Hz, 1H), 4.11 (t, J=5.5 Hz, 1H), 3.06 (s, 6H), 2.89 (t, J=5.5 Hz, 2H), 2.81 (s, 6H). $^{13}$C NMR (75 MHz, DMSO-$d_6$): δ 151.2, 136.2, 129.3, 128.9, 127.9, 127.7, 123.5, 119.1, 115.0, 102.4, 53.3, 44.9, 43.9. +ESI-HRMS: Calcd for $C_{16}H_{22}N_2O_4S$ $[M+H]^+$ 339.1373. found 339.1374.

N-(2-Oxoethyl)-5-(dimethylamino)naphthalene-1-sulfonamide

The acetal 11 (287 mg, 850 mop was dissolved in MeOH (1 mL) and coned HCl (0.5 mL) was added to the solution, which was stirred for 1 h at 25° C. The reaction mixture was then evaporated to dryness; the material left was dissolved in $CH_2Cl_2$ (10 mL) and the solution was washed with $NaHCO_3$ (2 mL of a saturated aqueous solution). The organic layer was collected and was evaporated under low pressure to give the aldehyde as a light green foam, the total amount of which was used without further purification in the preparation of 12.

The dansylated uridine conjugate 12

2'-O-(Aminooxymethyl)uridine (5a) was prepared from silica gel-purified 4a at a scale and under conditions identical to those described for the preparation of 8. After complete $NH_4F$-mediated desilylation and removal of the phthalimido group, a solution of all the N-(2-oxoethyl)-5-(dimethylamino)naphthalene-1-sulfonamide generated above in MeOH (1 mL) was added the reaction mixture, which was heated at 55±2° C. in a 4-mL screw-capped vial until completion of the oximation reaction (1 h) as indicated by TLC ($CHCl_3$/MeOH 9:1 v/v). The reaction mixture was then worked-up and processed exactly as described in the preparation of 8. The product was purified by chromatography on silica gel employing a gradient of MeOH (0→6%) in $CH_2Cl_2$ as the eluent. Fractions containing the pure product were collected, evaporated to dryness under reduced pressure to give 12 as a light green powder (82 mg, 140 µmol) in a yield of 70% based on the molar amount of starting material (4a) that was used. +ESI-HRMS: Calcd for $C_{24}H_{29}N_5O_9S$ $[M+H]^+$ 564.1759. found 564.1759.

N-(4,4-Diethoxybutyl)-5-(dimethylamino)naphthalene-1-sulfonamide (13)

To a solution of dansyl chloride (270 mg, 1.00 mmol) in $CH_2Cl_2$ (10 mL) was added 4-aminobutyraldehyde diethyl acetal (237 µL, 1.20 mmol) and $Et_3N$ (170 µL, 1.20 mmol). The solution was stirred for 1 h at 25° C. and was then evaporated to dryness under reduced pressure. The material left was processed and purified under conditions identical to those described for the processing and purification of 11. Fractions containing the product were collected and evaporated to dryness under low pressure affording 13 (366 mg, 930 µmol) as a solid in a yield of 93%. $^1$H NMR (300 MHz, DMSO-$d_6$): δ 8.45 (dt, J=8.5, 1.1 Hz, 1H), 8.30 (dt, J=8.8, 0.9 Hz, 1H), 8.09 (dd, J=7.3, 1.2 Hz, 1H), 7.89 (t, J=5.5 Hz, 1H), 7.61 (t, J=8.5 Hz, 1H), 7.58 (t, J=8.5 Hz, 1H), 7.25 (dd, J=7.6, 0.7 Hz, 1H), 4.19 (t, J=5.3 Hz, 1H), 3.36 (m, 2H), 3.23 (m, 2H), 2.81 (s, 6H), 2.77 (t, J=5.5 Hz, 2H), 1.31 (m, 4H), 0.99 (t, J=7.0 Hz, 6H). $^{13}$C NMR (75 MHz, DMSO-$d_6$): δ 151.2, 136.1, 129.2, 128.9, 128.1, 127.7, 123.5, 119.1, 114.9, 101.6, 60.2, 44.9, 42.2, 30.1, 24.4, 15.1. +ESI-HRMS: Calcd for $C_{20}H_{30}N_2O_4S$ $[M+H]^+$ 395.1999. found 395.2000.

N-(4-Oxobutyl)-5-(dimethylamino)naphthalene-1-sulfonamide

This aldehyde was prepared from acetal 13 at a scale and under conditions identical to those employed for the preparation N-(2-oxoethyl)-5-(dimethylamino)naphthalene-1-sulfonamide from acetal 11. N-(4-Oxobutyl)-5-(dimethylamino)naphthalene-1-sulfonamide was obtained as a light green foam, the total amount of which was used without further purification in the preparation of 14.

The dansylated uridine conjugate 14

This conjugate was prepared and purified exactly as reported from the preparation and purification of the dansylated uridine conjugate 12. The dansylated uridine conjugate 14 was isolated as a light green powder (96 mg, 0.16 mmol) in a yield of 81% based on the molar amount of starting material (4a) that was used. +ESI-HRMS: Calcd for $C_{26}H_{33}N_5O_9S$ [M+H]$^+$ 592.2072. found 592.2071.

N-(2,2-Dimethoxyethyl)-4-(dimethylamino)azobenzene-4'-sulfonamide (15)

To a solution of 4-(dimethylamino)azobenzene-4'-sulfonyl chloride (324 mg, 1.00 mmol) in $CH_2Cl_2$ (5 mL) was added aminoacetaldehyde dimethyl acetal (130 μL, 1.20 mmol) and $Et_3N$ (179 μL, 1.20 mmol). The solution was allowed to stir for 16 h at 25° C. The reaction mixture was evaporated to dryness under reduced pressure and the material left was purified by silica gel chromatography using a gradient of MeOH (0→2%) in $CH_2Cl_2$ as the eluent. Fractions containing the product were collected and evaporated to dryness under reduced pressure affording 14 (373 mg, 950 μmol) as a solid in a yield of 95%. $^1$H NMR (300 MHz, DMSO-d$_6$): δ 7.19 (m, 4H), 7.82 (d, J=9.3 Hz, 2H), 6.85 (d, J=9.3 Hz, 2H), 4.29 (t, J=5.4 Hz, 1H), 3.19 (s, 6H), 3.08 (s, 6H), 2.89 (t, J=5.6 Hz, 2H). $^{13}$C NMR (75 MHz, DMSO-d$_6$): δ 154.4, 153.0, 142.5, 140.5, 127.7, 125.3, 122.1, 111.5, 102.3, 53.3, 44.1, 39.8. +ESI-HRMS: Calcd for $C_{18}H_{24}N_4O_4S$ [M+H]$^+$ 393.1591. found 393.1596.

N-(2-Oxoethyl)-4-(dimethylamino)azobenzene-4'-sulfonamide

The acetal 15 (287 mg, 850 μmol) was dissolved in a solution of 10% (w/v) $I_2$ in acetone (10 mL). The resulting solution was stirred at 25° C. for 16 h and was then evaporated to dryness under reduced pressure. The material left was dissolved in $CH_2Cl_2$ (10 mL) and washed with an aqueous solution of 5% (w/v) sodium bisulfite (5 mL) followed by a saturated aqueous solution of $NaHCO_3$ (5 mL). The organic layer was collected and was evaporated to dryness under vacuum. The total amount of the orange product was used in the preparation of 16.

The Dabsylated Cytidine Conjugate 16

2'-O-(Aminooxymethyl)cytidine (5b) was prepared from silica gel-purified 4b (140 mg, 0.2 mmol) as described above for the preparation of 6b. After complete $NH_4F$-mediated desilylation and removal of the phthalimido group, a solution of all the N-(2-oxoethyl)-4-(dimethylamino)azobenzene-4'-sulfonamide produced above in MeOH (1 mL) was added the reaction mixture, which was heated at 55±2° C. in a 4-mL screw-capped vial until completion of the oximation reaction (1 h) as indicated by TLC (CHCl$_3$/MeOH 9:1 v/v). The reaction mixture was then worked-up and processed exactly as described in the preparation of 8. The product was purified by chromatography on silica gel eluted employing a gradient of MeOH (0→8%) in $CH_2Cl_2$ as the eluent. Fractions containing the pure product were collected, evaporated to dryness under reduced pressure providing 8 as an orange powder (74 mg, 0.12 mmol) in a yield of 61% based on the molar amount of starting material (4b) that was employed. +ESI-HRMS: Calcd for $C_{26}H_{32}N_8O_8S$ [M+H]$^+$ 617.2137. found 617.2134.

N-(4-Cyanobut-1-yl)-5-(dimethylamino)naphthalene-1-sulfonamide (18)

4-Aminobutyronitrile was prepared from the reaction of 4-chlorobutyronitrile (207 mg, 2.00 mmol) with potassium phthalimide (407 mg, 2.20 mmol) under the conditions described by McKay et al., *J. Am. Chem. Soc.*, 1959, 81, 4328-4335, with the following modification: the crude 4-aminobutyronitrile, instead of purified 4-aminobutyronitrile hydrochloride, was reacted with a stirred solution of dansyl chloride (135 mg, 500 μmol) in $CH_2Cl_2$ (1 mL) for 10 min at ~25° C. The reaction product was analyzed by TLC (CHCl$_3$/MeOH 95:5 v/v) and was purified by chromatography on silica gel using a gradient of MeOH (0→3%) in $CH_2Cl_2$ as the eluent. Fractions containing 18 were collected and evaporated under vacuum affording the pure product (123 mg, 390 μmol) in a yield of 78% based on the amount of dansyl chloride used in the reaction. $^1$H NMR (300 MHz, DMSO-d$_6$): δ 8.47 (dt, J=8.5, 1.1 Hz, 1H), 8.28 (dt, J=8.5, 1.1 Hz, 1H), 8.11 (dd, J=7.2, 1.2 Hz, 1H), 8.02 (t, J=5.8 Hz, 1H), 7.63 (t, J=7.5 Hz, 1H), 7.60 (t, J=7.5 Hz, 1H), 7.26 (dd, J=7.5, 0.7 Hz, 1H), 2.85 (m, 2H), 2.82 (s, 6H), 2.39 (t, J=7.0 Hz, 2H), 1.60 (quint, J=7.0 Hz, 2H). $^{13}$C NMR (75 MHz, DMSO-d$_6$): δ 151.3, 135.5, 129.5, 129.0, 128.9, 128.3, 127.8, 123.5, 119.9, 118.8, 115.1, 44.9, 40.9, 25.2, 13.4. +ESI-HRMS: Calcd for $C_{16}H_{19}N_3O_2S$ [M+H]$^+$ 318.1271. found 318.1271.

2'-O-[5-(dimethylamino)naphthalene-1-sulfonamidyl-N-oxymethyl]uridine (19)

Silica gel-purified 2'-O-(aminooxymethyl)uridine (5a, 87 mg, 0.3 mmol) was dissolved in pyridine (2 mL) and dansyl chloride (135 mg, 0.5 mmol) was added. The solution was stirred at ~25° C. for 2 h and was then evaporated to dryness under vacuum. The crude product 19 was purified by silica gel chromatography using a gradient of MeOH (0→8%) in $CH_2Cl_2$ as the eluent. Fractions containing 19 were collected and evaporated under vacuum giving a yellow solid in a yield of 83% (130 mg, 0.25 mmol) based on the molar amount of the starting material (5a) that was used. +ESI-HRMS: Calcd for $C_{22}H_{26}N_4O_9S$ [M+H]$^+$ 523.1493. found 523.1493.

General Procedure for the Removal of Reporter and Functional Groups from the Ribonucleosides 6a-d, 10, 12, 14 and 16.

Purified 6a (5 mg, 10 μmol) was placed in a 4-mL screw cap glass vial and 0.5 M TBAF in THF (100 μL) was added. The tightly closed vial was heated at 55° C.; progress of the reaction was determined by RP-HPLC. Excess solvent was removed under a stream of air; the material left was dissolved in HPLC buffer A (0.1 M triethylammonium acetate, pH 7.0, 500 μL). An aliquot (2 μL) was analyzed by RP-HPLC according to the following conditions for 6a-d, 12, 14 and 16: starting from 0.1 M triethylammonium acetate pH 7.0, a linear gradient of 1% MeCN/min was pumped at a flow rate of 1 mL/min for 40 min; the gradient was then increased to 6% MeCN/min for 10 min at the same flow rate and was kept isocratic for an additional 15 min. In the case of 10, the RP-HPLC conditions were: starting from 0.1 M triethylammonium acetate pH 7.0, a linear gradient of 1% MeCN/min is pumped at a flow rate of 1 mL/min for 40 min. Peak heights were normalized to the highest peak, which was set to 1 arbitrary unit.

Example 2

This Example illustrates a method of preparing oligonucleotides in accordance with an embodiment of the invention.

2'-O-(Methoxymethanimine-N-oxymethyl)uridine [20a (R=CH$_2$OCH$_3$)]

Purified 4a (2.0 g, 3.0 mmol) was dissolved in methanol (30 mL) to which was added ammonium fluoride (925 mg 25.0 mmol). The heterogeneous reaction mixture was stirred at ~45° C. until complete desilylation and dephthalimidation was obtained (~16 h) as indicated by TLC (CHCl$_3$/MeOH (9:1 v/v)). Without neither workup nor purification, 2-methoxyacetaldehyde, which was generated in situ in a separate container by mixing 2-methoxyacetaldehyde dimethylacetal (1.2 g, 10 mmol,) and concd HCl (500 µL) in 50% aqueous methanol (5 mL) over a period of 2 h at ~25° C., was added in its totality to the reaction mixture containing 2'-O-aminooxymethyluridine. The oximation reaction was allowed to proceed for 1 h at ~45° C. The reaction mixture was then evaporated to dryness under reduced pressure, dissolved/suspended in 10 mL $CHCl_3/MeOH/H_2O$ (1:8:1, v/v/v), mixed with silica gel (~10 g) and allowed to air dry overnight at ~25° C. The dried silica gel mix gel was evenly distributed on the top of a column packed with silica gel (100 g) pre-equilibrated in $CH_2Cl_2$. The product was eluted from the column employing a gradient of MeOH (0→8%) in $CH_2Cl_2$ as the eluent. Fractions containing the pure product (TLC) were collected, evaporated to dryness under reduced pressure affording 26a (R=$CH_2OCH_3$) as a white powder (770 mg, 2.22 mmol) in a yield of 74% based on 4a.

Preparation of 20a (R=H, $CH_3$, $CH_2F$, $CH_2Cl$, $CH_2Br$ and $CH_2SCH_3$)

These compounds were prepared and purified under conditions similar to that of 20a (R=$CH_2OCH_3$) with the exception of replacing 2-methoxyacetaldehyde with formaldehyde, acetaldehyde, 2-fluoroacetaldehyde, 2-chloroacetaldehyde, 2-bromoacetaldehyde and 2-methylthioacetaldehyde. 20a (R=H, $CH_3$, $CH_2F$, $CH_2Cl$, $CH_2Br$ and $CH_2SCH_3$) were obtained in yields similar to that of 20a (R=$CH_2OCH_3$).

Preparation of 20a (R=$CH_2CN$)

This compound was prepared by the reaction of 20a (R=$CH_2Cl$ or $CH_2Br$) with tetra-n-butylammonium cyanide in methanol. 20a (R=$CH_2CN$) was purified under conditions similar to that of 20a (R=$CH_2OCH_3$).

Preparation of 20a (R=$CH_2S(O)CH_3$)

This compound was prepared by oxidation of 20a (R=$CH_2SCH_3$) using 30% $H_2O_2$ (3 mL) over a period of 10 min at ~25° C. The reaction product was purified by chromatography on silica gel, as described for 20a (R=$CH_2OCH_3$) using a gradient of MeOH (0→10%) in $CH_2Cl_2$ as the eluent. The ribonucleoside 20a (R=$CH_2S(O)CH_3$) was isolated in a yield of 93%.

Preparation of 20a (R=$CH_2SO_2CH_3$)

This compound was prepared by oxidation of 20a (R=$CH_2SCH_3$) using m-chloroperbenzoic acid over a period of 2 h at ~25° C. in $CH_2Cl_2$. The reaction product was purified by chromatography on silica gel, as described for 20a (R=$CH_2S(O)CH_3$) using a gradient of MeOH (0→10%) in $CH_2Cl_2$ as the eluent. The ribonucleoside 20a (R=$CH_2SO_2CH_3$) was isolated in a yield of 62%.

Preparation of 2-chloro-2,2-dimethylbutyraldehyde

This compound was prepared from isobutyraldehyde and sulfuryl chloride according to a literature procedure and was purified by distillation (Stevens, C. L.; Gillis, B. T. *J. Am. Chem. Soc.* 1956, 79, 3448-3451).

Preparation of 2-bromo-2,2-dimethylbutyraldehyde dimethylacetal

This compound was prepared from isobutyraldehyde and N-bromosuccinimide according to a literature procedure and was purified by vacuum distillation (Marvell, E. N.; Joncich, M. J. *J. Am. Chem. Soc.* 1951, 73, 973-975).

Preparation of 2-cyano-2,2-dimethylbutyraldehyde

This compound was prepared from 2-chloro-2,2-dimethylbutyraldehyde according to a literature procedure (Reetz, M. T; Chatziiosifidis, I.; Künzer, H.; Müller-Starke, H. *Tetrahedron* 1983, 39, 961-965) or from malononitrile according to a literature procedure (Maraval. A.; Igau, A.; Donnadieu, B.; Majoral, J.-P. *Eur. J. Org. Chem.* 2003, 385-394.

Preparation of 2-methylthio-2,2-dimethylbutyraldehyde dimethylacetal

This compound was prepared by the reaction of 2-bromo-2,2-dimethylbutyraldehyde dimethylacetal with sodium thiomethoxide in aqueous ethanol.

Preparation of 2-methylsulfinyl-2,2-dimethylbutyraldehyde dimethylacetal

This compound was prepared by the reaction of 2-methylthio-2,2-dimethylbutyraldehyde dimethylacetal using 30% $H_2O_2$ over a period of 10 min at ~25° C.

Preparation of 2-methylsulfonyl-2,2-dimethylbutyraldehyde dimethylacetal

This compound was prepared by the reaction of 2-methylthio-2,2-dimethylbutyraldehyde dimethylacetal using m-chloroperbenzoic acid over a period of 2 h at ~25° C. in $CH_2Cl_2$.

Preparation of 20a (R=$C(CH_3)_2CN$, $C(CH_3)_2SCH_3$, $C(CH_3)_2S(O)CH_3$ and $C(CH_3)_2SO_2CH_3$)

These compounds were prepared and purified under conditions similar to that of 20a (R=$CH_2OCH_3$) with the exception of replacing 2-methoxyacetaldehyde with 2-cyano-2,2-dimethylbutyraldehyde, 2-methylsulfinyl-2,2-dimethylbutyraldehyde and 2-methylsulfonyl-2,2-dimethylbutyraldehyde, which with the exception of 2-cyano-2,2-dimethylbutyraldehyde, were generated in situ in a separate container by mixing each of the corresponding dimethylacetal and concd HCl in 50% aqueous methanol over a period of 2 h at ~25° C.

5'-O-(4,4'-Dimethoxytrityl)-2'-O-(methoxymethanimine-N-oxymethyl)uridine [21a (R=$CH_2OCH_3$)]

To a solution of dry ribonucleoside 20a (R=$CH_2OCH_3$) (2.0 mmol) in anhydrous pyridine (15 mL) was added 4,4'-dimethoxytrityl chloride (2.2 mmol). The solution was stirred at ~25° C. and progress of the reaction was monitored by TLC ($CHCl_3$/MeOH (95:5 v/v)) until completion (~2 h). The reaction mixture was then poured into a saturated solution of $NaHCO_3$ (200 mL) and was extracted with $CH_2Cl_2$ (3×150 mL). The combined organic layers were dried over anhydrous $Na_2SO_4$. Following filtration, the filtrate was evaporated under reduced pressure and was co-evaporated with toluene (3×100 mL). The crude product was purified by silica gel chromatography using a gradient of $CH_3OH$ (0→2%) in $CH_2Cl_2$ containing 0.2% (v/v) triethylamine. Fractions containing pure 26a were collected and rotoevaporated to a foam under low pressure. Ribonucleoside 21a (R=$CH_2OCH_3$) was dissolved in dry $C_6H_6$ (10 mL); the resulting solution was frozen and then lyophilized under high vacuum to produce a yellowish powder in a yield of 89%.

Preparation of 21a (R=H, —CH$_2$F, —CH$_2$CN, —CH$_2$OCH$_3$, —CH$_2$SCH$_3$, —CH$_2$S(O)CH$_3$, —CH$_2$SO$_2$CH$_3$, —C(CH$_3$)$_2$CN, —C(CH$_3$)$_2$SCH$_3$, —C(CH$_3$)$_2$S(O)CH$_3$ or —C(CH$_3$)$_2$SO$_2$CH$_3$). These compounds were prepared and purified under condition identical to that of 21a (R=CH$_2$OCH$_3$) and were isolated in yields of 85-95%.

5'-O-(4,4'-Dimethoxytrityl)-3'-O—[(N,N-diisopropylamino) (2-cyanoethyl)]phosphinyl-2'-O-(methoxymethanimine-N-oxymethyl)uridine [22a (R=CH$_2$OCH$_3$)]. To a solution of ribonucleoside 21a (R=CH$_2$OCH$_3$) (1.0 mmol) in anhydrous CH$_2$Cl$_2$ (5.0 mL) containing Et$_3$N (0.70 mL, 5.0 mmol) was added 2-cyanoethyl N,N-diisopropylchlorophosphoramidite (525 µL, 2.00 mmol). The reaction mixture was stirred at ~25° C. under argon until complete disappearance of the starting material (~2 h) was observed by TLC (C$_6$H$_6$/Et$_3$N (9:1 v/v)). The reaction mixture was then poured into a saturated solution of NaHCO$_3$ (50 mL) and was extracted with CH$_2$Cl$_2$ (2×100 mL). The combined organic layers were dried over anhydrous Na$_2$SO$_4$ and then filtered. The filtrate was evaporated to dryness under reduced pressure. The crude product was purified by silica gel chromatography using C$_6$H$_6$/Et$_3$N (9:1 v/v) as the eluent. Fractions containing the pure product (TLC) were pooled together and evaporated to dryness under vacuum. The material was dissolved in dry C$_6$H$_6$ (3 mL) and the resulting solution was added to stirred cold (~78° C.) hexane (100 mL). Pure phosphoramidite 22a precipitated immediately as a white solid. After careful decantation of hexane, the solid was dissolved in dry C$_6$H$_6$ (10 mL). The solution was frozen and then lyophilized under high vacuum affording Et$_3$N-free 22a (R=CH$_2$OCH$_3$) in a yield of 90%.

Preparation of 22a (R=H, —CH$_2$F, —CH$_2$CN, —CH$_2$OCH$_3$, —CH$_2$SCH$_3$, —CH$_2$S(O)CH$_3$, —CH$_2$SO$_2$CH$_3$, —C(CH$_3$)$_2$CN, —C(CH$_3$)$_2$SCH$_3$, —C(CH$_3$)$_2$S(O)CH$_3$ or —C(CH$_3$)$_2$SO$_2$CH$_3$). These compounds were prepared and purified under condition identical to that of 22a (R=CH$_2$OCH$_3$) with the exception that MeCN/Et$_3$N (9:1 v/v) was required to elute 22a (R=CH$_2$S(O)CH$_3$ and CH$_2$SO$_2$CH$_3$) off the silica gel chromatography column. These ribonucleoside phosphoramidites were isolated in yields of 85-95%.

Solid-Phase Oligonucleotide Synthesis.

Solid phase synthesis of r(Up)$_{20}$dT, where dT stands for 2'-deoxythymidine, was conducted on a scale of 0.2 µmol in the "trityl-off" mode using a succinyl long chain alkylamine controlled-pore glass support functionalized with 5'-O-DMTr-dT as the leader nucleoside. The syntheses were carried out using a DNA/RNA synthesizer and either phosphoramidite 22a (R=CH$_2$OCH$_3$) or 22a (R=CH$_2$S(O)CH$_3$). The ribonucleoside phosphoramidites were dissolved in dry MeCN to give 0.2 M solutions. 5-Ethylthio-1H-tetrazole was employed for phosphoramidite activation and used as a 0.25 M solution in dry MeCN. All other ancillary reagents necessary for the preparation of oligonucleotides were purchased and utilized as recommended by the manufacturer. The reaction time for each phosphoramidite coupling step was 180 s. The dedimethoxytritylation and capping steps of the synthesis cycle were carried out, each, over a period of 60 s. For comparison purpose, the solid-phase synthesis of r(Up)$_{20}$dT was also performed using commercial 2'-O-TBDMS uridine phosphoramidite under synthesis and deblocking conditions similar to those reported in the literature (Ogilvie, K. K.; Usman, N.; Nicoghosian, K.; Cedergren, R. *J. Proc. Natl. Acad. Sci. U.S.A.* 1988, 85, 5764-5768).

Deprotection and Characterization of Oligonucleotides Synthesized from Phosphoramidite 22a (R=CH$_2$S(O)CH$_3$).

Figures 13A, 13B:
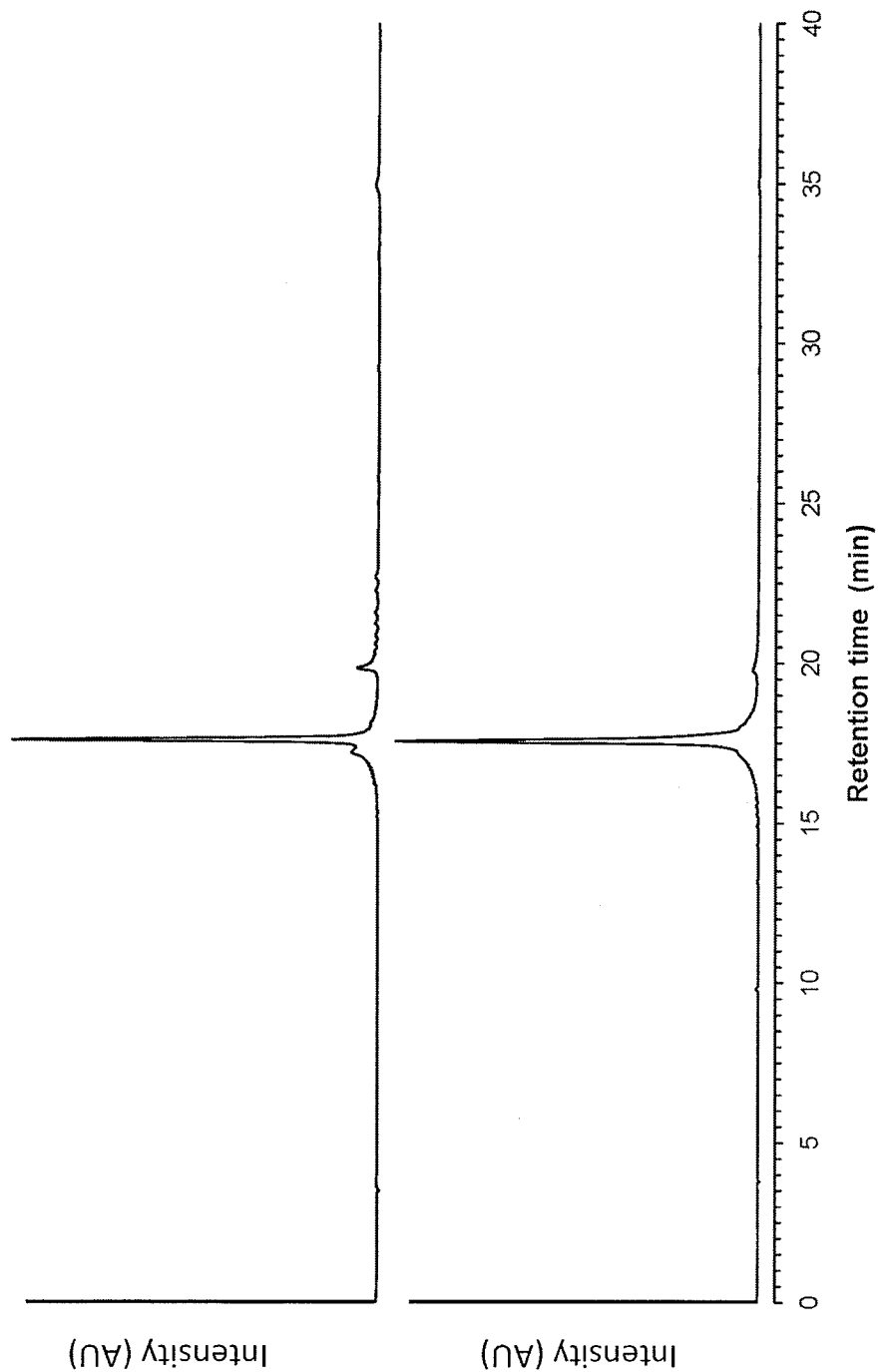
FIG. 13A depicts the RP-HPLC chromatogram of unpurified desalted r(Up)$_{20}$dT prepared from the commercial 2'-O-TBDMS uridine phosphoramidite under the synthesis and deblocking conditions reported in the literature.
FIG. 13B depicts the RP-HPLC chromatogram of unpurified desalted r(Up)$_{20}$dT prepared from the ribonucleoside 22a (R=$CH_2S$ (O)CH₃) under the synthesis and deblocking conditions described in Example 2 [0136-0137].

The solid-phase-linked 5'-dedimethoxytritylated oligonucleotide was placed into a 4 mL screw-capped glass vial to which was added concd NH$_4$OH (1 mL). The suspension was shaken occasionally over a period of 30 min. The ammoniacal solution was transferred to a 4 mL glass vial and evaporated to dryness using a stream of air. The oligonucleotide was then dissolved in 0.5 M tetrabutylammonium fluoride in DMSO (100 µL) and heated at 55° C. for 48 h. The solution was loaded on a PD-10 column pre-packed Sephadex G-25M that was equilibrated in ddH$_2$O. The oligonucleotide was eluted from the column using ddH$_2$O as the eluent. Fractions (1-mL) were collected and those fractions containing the oligonucleotide (UV$_{260}$) were pooled together. RP-HPLC analysis of the desalted oligonucleotide was performed using a 5 µm Supelcosil LC-18S column (25 cm×4.6 mm) according to the following conditions: starting from 0.1 M triethylammonium acetate pH 7.0, a linear gradient of 1% MeCN/min was pumped at a flow rate of 1 mL/min for 40 min and was then held, isocratically, for 10 min. A chromatogram of unpurified and desalted r(Up)$_{20}$dT is shown in FIG. 13B. MALDI-TOF MS: Calcd for C$_{190}$H$_{214}$N$_{42}$O$_{165}$P$_{20}$ [M–H]$^-$ 6344. found 6349.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (I):

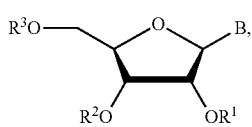

wherein B is an optionally protected nucleobase;

$R^1$, $R^2$, and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, a linker-attached solid support, and a group of formula:

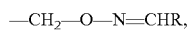

wherein R is selected from the group consisting of —CH$_2$F, —CH$_2$Cl, —CH$_2$Br, —CH$_2$CN, —CH$_2$OCH$_3$, —CH$_2$SCH$_3$, —CH$_2$S(O)CH$_3$, —CH$_2$SO$_2$CH$_3$, —CH(CH$_3$)F, —CH(CH$_3$)CN, —C(CH$_3$)$_2$CN, —CH(CH$_3$)OCH$_3$, —CH(CH$_3$)SCH$_3$, —CH(CH$_3$)S(O)CH$_3$, —C(CH$_3$)$_2$S(O)CH$_3$, —C(CH$_3$)$_2$SO$_2$CH$_3$, —CH(CH$_3$)SO$_2$CH$_3$, —C(CH$_3$)$_2$Cl, —C(CH$_3$)$_2$Br, —CY(Z)F, —CY(Z)CN, —CY(Z)OCH$_3$, —CY(Z)SCH$_3$, —CY(Z)S(O)CH$_3$, and —CY(Z)SO$_2$CH$_3$, wherein Y is F or CH$_3$ and Z is F or CH$_3$, or wherein the —N═CHR portion of —CH$_2$—O—N═CHR forms an imine moiety of one of the following formulas:

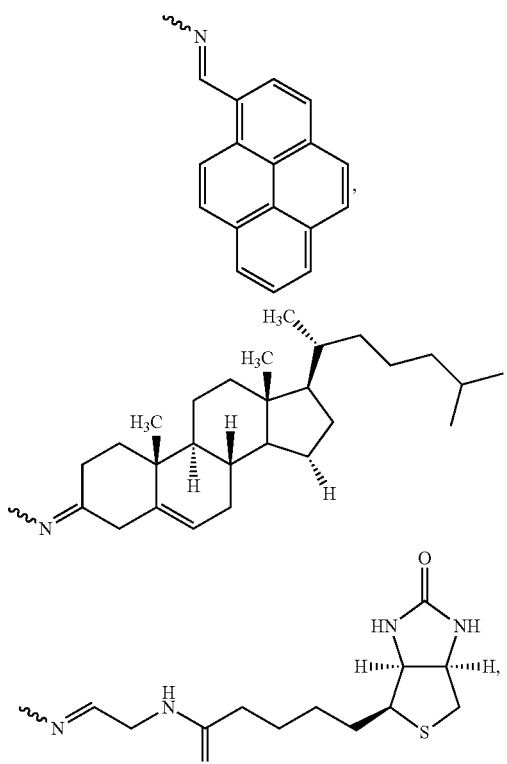

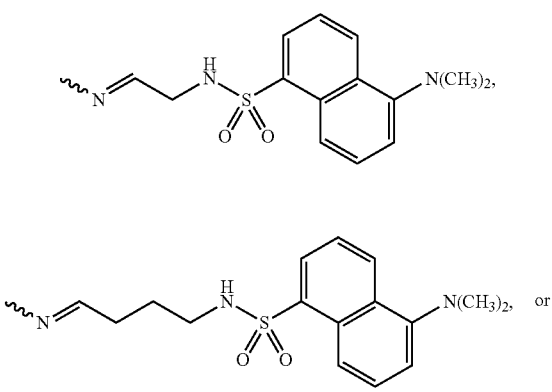

-continued

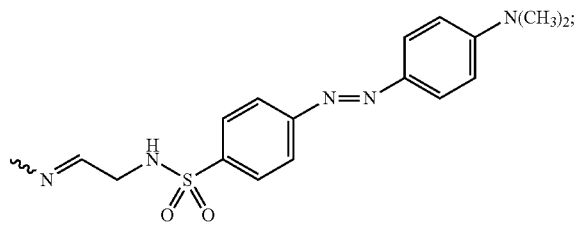

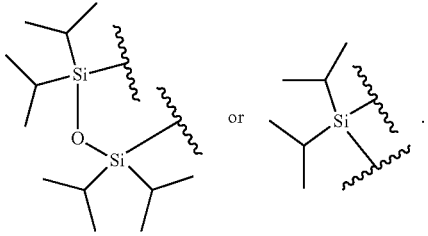

or R² and R³ together form a hydroxyl protecting ring;
wherein at least one of R¹, R², and R³ is —CH₂—O—N=CHR.

2. The compound of claim 1, wherein the optionally protected nucleobase or the nucleobase is selected from the group consisting of cytosine, adenine, guanine, uracil, thymine, xanthine, hypoxanthine, alkyl derivatives thereof, amino derivatives thereof, halo derivatives thereof, 8-aminoadenine, 2- or 8-alkyladenine, 5-halouracil, 5-halocytosine, 2,6-diaminopurine, 6-azauracil, 4-thiouracil, 5-trifluoromethyluracil, 5-trifluoromethylcytosine, 6-azathymine, 6-thioguanine, 7-deazaadenine, 7-deazaguanine, 8-mercaptoadenine, 8-alkylthioadenine, 8-hydroxy/oxoadenine, 8-mercaptoguanine, 8-alkylthioguanine, 8-hydroxy/oxoguanine, 1-methyladenine, 2-methyladenine, $N^6$-methyladenine, $N^6$-isopentyladenine, 2-methylthio-$N^6$-isopentyladenine, $N^6,N^6$-dimethyladenine, 8-bromoadenine, 2-thiocytosine, 3-methylcytosine, 5-methylcytosine, 5-ethylcytosine, $N^4$-acetylcytosine, 1-methylguanine, $N^2$-methylguanine, 7-methylguanine, $N^2,N^2$-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxymethyl)uracil, 5-(methylaminomethyl)uracil, 5-(carboxymethylaminomethyl)uracil, 2-thiouracil, 5-methyl-2-thiouracil, 5-(2-bromovinyl)uracil, uracil-5-oxyacetic acid, uracil-5-oxyacetic acid methyl ester, 2-aminopurine, 6-hydroxyaminopurine, and 6-thiopurine.

3. The compound of claim 1, wherein the optionally protected nucleobase is a nucleobase whose exocyclic amino group is protected to form a labile protecting group selected from an amide moiety, imide moiety, carbamate moiety, trityl moiety, and amidine moiety.

4. The compound of claim 3, wherein the protecting group forms an amide moiety, carbamate moiety, amidine moiety, or trityl moiety.

5. The compound of claim 4, wherein the amide moiety is a trifluoroacetyl amide moiety, acetyl amide moiety, phenoxyacetyl amide moiety, tert-butylphenoxyacetyl amide moiety, benzoyl amide moiety, or isobutyryl amide moiety.

6. The compound of claim 3, wherein the protecting group forms a carbamate moiety.

7. The compound of claim 6, wherein the carbamate moiety is a tert-butoxycarbonyl carbamate moiety, (4-nitrophenyl)ethyloxy carbonyl carbamate moiety, or N-benzyloxycarbonyl carbamate moiety.

8. The compound of claim 1, wherein R² and R³ together form a hydroxyl protecting ring or R² and R³ are hydroxyl protecting groups.

9. The compound of claim 8, wherein the hydroxyl protecting ring or hydroxyl protecting group is of the formula:

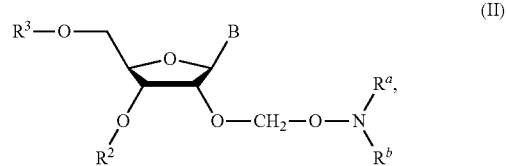

10. The compound of claim 1, wherein the hydroxyl protecting group is a silyl ether group selected from the group consisting of tert-butyldimethylsilyl, tert-butyldiphenylsilyl, dimethylphenylsilyl, and diphenylmethylsilyl, benzyloxycarbonyl, trityl, methoxytrityl, 4,4'-dimethoxytrityl, alkylcarbonyl, alkyloxycarbonyl, pixyl, tert-butyloxycarbonyl, or 9-fluorenylmethoxycarbonyl (Fmoc).

11. The compound of claim 1, wherein R³ is a linker-attached solid support.

12. The compound of claim 1, wherein (i) R² is dimethoxytrityl; (ii) R² and R³ are H; or (iii) R² and/or R³ is a nucleic acid moiety which is an oligonucleotide linked through a phosphotriester, phosphodiester, phosphorothioate triester, phosphorothioate diester or a phosphoramidate linkage.

13. A method of preparing a compound of formula II:

(II)

$$R^3-O-\overset{}{\underset{R^2}{\diagdown}}\overset{O}{\diagup}\overset{B}{\diagdown}\overset{R^a}{\underset{O-CH_2-O-N\diagdown R^b}{}},$$

wherein B is an optionally protected nucleobase;

$R^a$ and $R^b$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, and amido, or $R^a$ and $R^b$ together with the N form a group of the formula: =CHR, wherein R is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyano(halo)alkyl, alkoxy(halo)alkyl, aryloxy(halo)alkyl, alkylthio(halo)alkyl, arylthio(halo)alkyl, alkylsulfinyl(halo)alkyl, arylsulfinyl(halo)alkyl, alkylsulfonyl(halo)alkyl and arylsulfonyl(halo)alkyl; and $R^2$ and $R^3$ are independently selected from the group consisting of H, $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkyl, heterocyclyl $C_1$-$C_6$ alkyl, heterocyclyl, heteroaryl, a hydroxyl protecting group, a nucleic acid moiety, a nucleotide moiety, and a linker-attached solid support;

the method comprising:

(i) converting the f-OH group of the compound of formula (III):

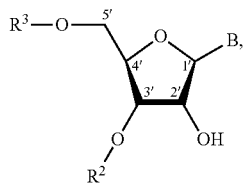

(III)

to a 2'-methylthiomethoxy group of a compound of formula (IV):

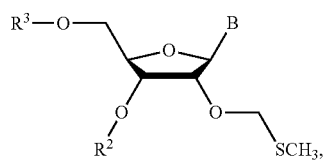

(IV)

(ii) converting the 2'-methylthiomethoxy group to a 2'-chloromethoxy group to obtain a compound of formula (V):

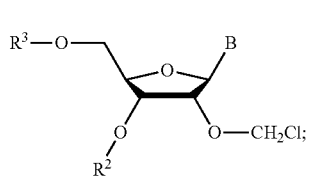

(V)

(iii) converting the 2'-chloromethoxy group of the compound of formula (V) to obtain a compound of the formula (VI);

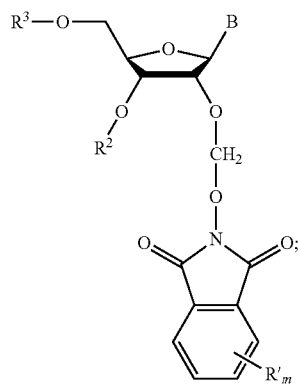

(VI)

wherein R' is H or a substituent selected from the group consisting of halo, hydroxy, cyano, formyl, acyl, alkyl carbonyl, carboxyl, phosphoryl, $C_1$-$C_6$ alkyl phosphonyl, cyano, nitro, alkoxy, alkylthio, acyl, acyloxy, thioacyl, acylthio, aryloxy, amino, alkylamino, dialkylamino, aldehydo, ureido, aminocarbonyl, $C_1$-$C_6$ alkyl, halo $C_1$-$C_6$ alkyl, hydroxy $C_1$-$C_6$ alkyl, $C_2$-$C_6$ alkenyl, $C_3$-$C_8$ cycloalkyl, $C_3$-$C_8$ cycloalkyl $C_1$-$C_6$ alkyl, $C_3$-$C_8$ cycloalkenyl, $C_6$-$C_{14}$ aryl, and $C_6$-$C_{14}$ aryl $C_1$-$C_6$ alkyl; and m is 1 to 4;

(iv) reacting the compound of formula (VI) with ammonium fluoride to obtain a compound of formula VII, in situ,

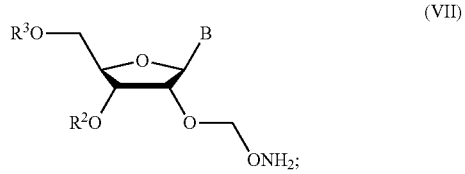

(VII)

and (v) reacting the compound of formula VII with a compound having an aldehyde or ketone group to obtain a compound of formula (II).

14. A method for preparing an oligoribonucleotide of chain length n, where n is the number of nucleotide residues in the oligoribonucleotide, wherein n is an integer of 2 to 200, the method comprising:

(i) providing a substrate comprising a nucleoside protected at the 2'-hydroxy function with an aminooxymethyl-derived protecting group and a solid support covalently linked to its 3'-hydroxy function, said substrate having the formula (IX):

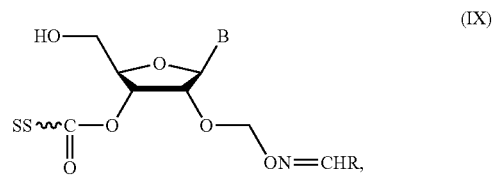

(IX)

wherein B is an optionally protected nucleobase;
R is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyano(halo)alkyl, alkoxy(halo)alkyl, aryloxy(halo)alkyl, alkylthio(halo)alkyl, arylthio(halo)alkyl, alkylsulfinyl(halo)alkyl, arylsulfinyl(halo)alkyl, alkylsulfonyl(halo)alkyl and arylsulfonyl(halo)alkyl;
and SS is a linker-attached solid support;

(ii) providing a 5'-OH-protected nucleoside phosphoramidite derivative of formula (X):

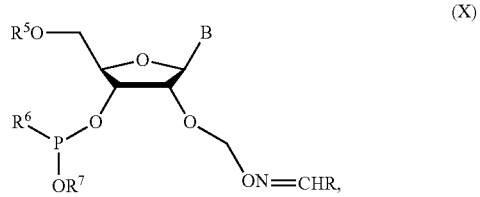

(X)

wherein $R^5$ is a hydroxyl protecting group; $R^6$ is an N,N-dialkylamino group or a saturated heterocyclic group having at least one nitrogen atom, optionally with one or more heteroatoms selected from the group consisting of O and S; and $OR^7$ is a phosphorus protecting group;

(iii) coupling the derivative of formula (X) with the substrate of formula (IX) to obtain a product comprising the substrate coupled to the derivative of formula (X);

(iv) 5'-capping any unreacted substrate of formula (IX) from step (iii);
(v) oxidizing the phosphite triester function present in the product of step (iii) to obtain a substrate having a protected phosphate triester function;
(vi) deprotecting the 5'-hydroxy group of the product of step (v);
(vii) repeating steps (iii)-(vi) n−1 times to build a protected oligonucleotide chain containing "n" nucleotide residues on the linker-attached solid support;
(viii) removing the nucleobase and phosphate protecting groups and cleaving the oligonucleotide from the linker-attached solid support; and
(ix) optionally deprotecting the 2'-OH group.

15. A method for preparing an oligoribonucleotide of chain length n, where n is the number of nucleotide residues in the oligoribonucleotide, wherein n is an integer of 2 to 200, the method comprising:

(i) providing a substrate comprising a nucleoside protected at one of the 2'-, 3'-, or 5'-hydroxy function with an aminooxymethyl-derived protecting group and a solid support covalently linked to one of the remaining hydroxy functions, said substrate having the formula (XI):

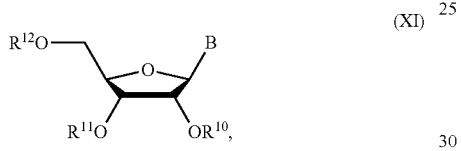

(XI)

wherein B is an optionally protected nucleobase;
wherein at least one of $R^{10}$ and $R^{11}$ is an aminooxymethyl-derived protecting group and the other of $R^{10}$ and $R^{11}$ is a linker-attached solid support, optionally linked through a carbonyl (>C=O) group; and $R^{12}$ is H;

(ii) providing a 5'-OH-protected nucleoside phosphoramidite derivative of formula (XII):

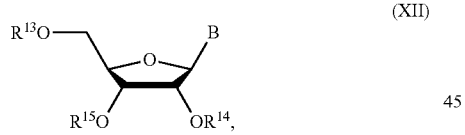

(XII)

wherein:
$R^{13}$ is a hydroxyl protecting group;
$R^{14}$ is an aminooxymethyl-derived protecting group of the formula —$CH_2$—O—N=$CHR^{16}$ and $R^{15}$ is a phosphoramidite group, if $R^{10}$ of the substrate of formula (XI) is an aminooxymethyl-derived protecting group and $R^{11}$ is a linker-attached solid support, optionally linked through a carbonyl (>C=O) group; or
$R^{15}$ is an aminooxymethyl-derived protecting group of the formula —$CH_2$—O—N=$CHR^{16}$ and $R^{14}$ is a phosphoramidite group, if $R^{11}$ of the substrate of formula (XI) is an aminooxymethyl-derived protecting group and $R^{10}$ is a linker-attached solid support, optionally linked through a carbonyl (>C=O) group;
wherein $R^{16}$ is selected from the group consisting of H, alkyl, haloalkyl, cyanoalkyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl, cyano(halo)alkyl, alkoxy(halo)alkyl, aryloxy(halo)alkyl, alkylthio(halo)alkyl, arylthio(halo)alkyl, alkylsulfinyl(halo)alkyl, arylsulfinyl(halo)alkyl, alkylsulfonyl(halo)alkyl and arylsulfonyl(halo)alkyl;
wherein the phosphoramidite group is of the formula: —$P(R^{17})(OR^{18})$, wherein $R^{17}$ is a N,N-dialkylamino group or a saturated heterocyclic group having at least one nitrogen atom, optionally with one or more heteroatoms selected from the group consisting of O and S; and $OR^{18}$ is a phosphorus protecting group;

(iii) coupling the derivative of formula (XII) with the substrate of formula (XI) to obtain a product comprising the substrate coupled to the derivative of formula (XII);
(iv) 5'-capping of unreacted substrate of formula (XI) from step (iii);
(v) oxidizing the phosphite triester function present in the product of step (iii) to obtain a product having a protected phosphate triester function;
(vi) deprotecting the 5'-hydroxy group of the product of step (v);
(vii) repeating steps (iii)-(vi) n−1 times to build a protected oligonucleotide chain containing "n" nucleotide residues on the linker-attached solid support;
(viii) removing the nucleobase and phosphate protecting groups and cleaving the oligonucleotide from the linker-attached solid support; and
(ix) optionally deprotecting the 2'-OH group or the 3'-OH group.

* * * * *

SEQUENCE LISTING

```
<160> NUMBER OF SEQ ID NOS: 1

<210> SEQ ID NO 1
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_structure
<222> LOCATION: (1)..(1)
<223> OTHER INFORMATION: Wherein n is 2'-deoxythymidine

<400> SEQUENCE: 1
nuuuuuuuuu uuuuuuuuuu                                              20
```